US010843041B1

(12) United States Patent
Cobb et al.

(10) Patent No.: US 10,843,041 B1
(45) Date of Patent: Nov. 24, 2020

(54) ACTUATOR-BASED EXERCISE AND TRAINING DEVICE

(71) Applicants: Tyson Cobb, Pensacola, FL (US);
Travis Craig, Pensacola, FL (US);
Jeremy Gines, Pensacola, FL (US);
Peter Neuhaus, Pensacola, FL (US)

(72) Inventors: Tyson Cobb, Pensacola, FL (US);
Travis Craig, Pensacola, FL (US);
Jeremy Gines, Pensacola, FL (US);
Peter Neuhaus, Pensacola, FL (US)

(73) Assignee: Florida Institute for Human and Machine Cognition, Inc., Pensacola, FL (US)

( * ) Notice: Subject to any disclaimer, the term of this patent is extended or adjusted under 35 U.S.C. 154(b) by 0 days.

(21) Appl. No.: 16/421,780

(22) Filed: May 24, 2019

(51) Int. Cl.
*A63B 24/00* (2006.01)
*A63B 21/00* (2006.01)
*A63B 21/04* (2006.01)
*A63B 21/02* (2006.01)
*A63B 23/12* (2006.01)
*A63B 23/035* (2006.01)

(52) U.S. Cl.
CPC ........ *A63B 24/0087* (2013.01); *A63B 21/023* (2013.01); *A63B 21/0428* (2013.01); *A63B 21/156* (2013.01); *A63B 21/4033* (2015.10); *A63B 23/03525* (2013.01); *A63B 23/1281* (2013.01); *A63B 24/0062* (2013.01); *A63B 2024/0093* (2013.01); *A63B 2220/51* (2013.01); *A63B 2220/54* (2013.01); *A63B 2220/833* (2013.01)

(58) Field of Classification Search
CPC .................. A63B 24/0087; A63B 1/00; A63B 21/4047–4049; A63B 23/0405–2023/0411; A63B 23/1209–1236; A63B 23/1281; A63B 21/078–0783; A63B 21/0058–0059
See application file for complete search history.

(56) References Cited

U.S. PATENT DOCUMENTS

| | | | | |
|---|---|---|---|---|
| 5,100,128 A | * | 3/1992 | Mabry | A63B 21/0632 482/134 |
| 5,116,297 A | * | 5/1992 | Stonecipher | A63B 21/0615 482/137 |
| 5,151,072 A | * | 9/1992 | Cone | A63B 21/078 482/104 |
| 7,101,327 B1 | * | 9/2006 | Baumler | A63B 21/078 482/100 |
| 7,452,311 B2 | * | 11/2008 | Barnes | A63B 21/00072 482/137 |
| 9,814,920 B1 | * | 11/2017 | Monterrey | A63B 21/4035 |
| 9,849,328 B1 | * | 12/2017 | Fulks | A61H 1/0266 |
| 10,065,060 B2 | * | 9/2018 | Simmons | A63B 21/0724 |
| 2014/0073492 A1 | * | 3/2014 | Hunter | A63B 21/4047 482/98 |
| 2014/0213414 A1 | * | 7/2014 | Balandis | G10L 15/22 482/5 |
| 2017/0080277 A1 | * | 3/2017 | Rogers | A63B 21/0783 |
| 2019/0175985 A1 | * | 6/2019 | Chapman | A63B 24/0062 |
| 2020/0070005 A1 | * | 3/2020 | Lin | A63B 21/078 |
| 2020/0188719 A1 | * | 6/2020 | Brand | A63B 21/00076 |

* cited by examiner

*Primary Examiner* — Jennifer Robertson
(74) *Attorney, Agent, or Firm* — J. Wiley Horton

(57) ABSTRACT

An exercise device where force is applied by computer-controlled actuators. The programmable nature of the force application allows the device to simulate weight-training devices and other useful exercise devices.

20 Claims, 24 Drawing Sheets

ACTUATOR-BASED EXERCISE AND TRAINING DEVICE

STATEMENT REGARDING FEDERALLY SPONSORED RESEARCH OR DEVELOPMENT

Funding for a portion of the development of this invention was provided by the National Aeronautics and Space Administration.

CROSS-REFERENCES TO RELATED APPLICATIONS

Not applicable

MICROFICHE APPENDIX

Not Applicable

BACKGROUND OF THE INVENTION

1. Field of the Invention

The present invention pertains to the field of physical exercise equipment. More specifically, the invention comprises a powered device that can apply force to the body in a controlled manner. The invention can mimic the forces applied by free weights in established forms of exercise. The invention can also apply unconventional forces that would not be possible using free weights or other existing exercise equipment.

2. Description of the Related Art

Prior art exercise devices tend to use weights or resistance schemes. Such devices are inherently limited in the type of forces they can apply. In addition, such devices are often quite heavy. The present invention seeks to overcome these known disadvantages of the prior art devices, as well as providing other additional advantages.

BRIEF SUMMARY OF THE INVENTION

The present invention comprises an exercise device where force is applied by computer-controlled actuators. The programmable nature of the force application allows the device to simulate weight-training devices and other useful exercise devices. The invention also includes reaction force measurement. In a preferred embodiment the user is in a standing position and the reaction forces produced by the user's feet are monitored. A control system is used to monitor stability so that the forces can be altered if the user enters an unbalanced state.

Figure 1:
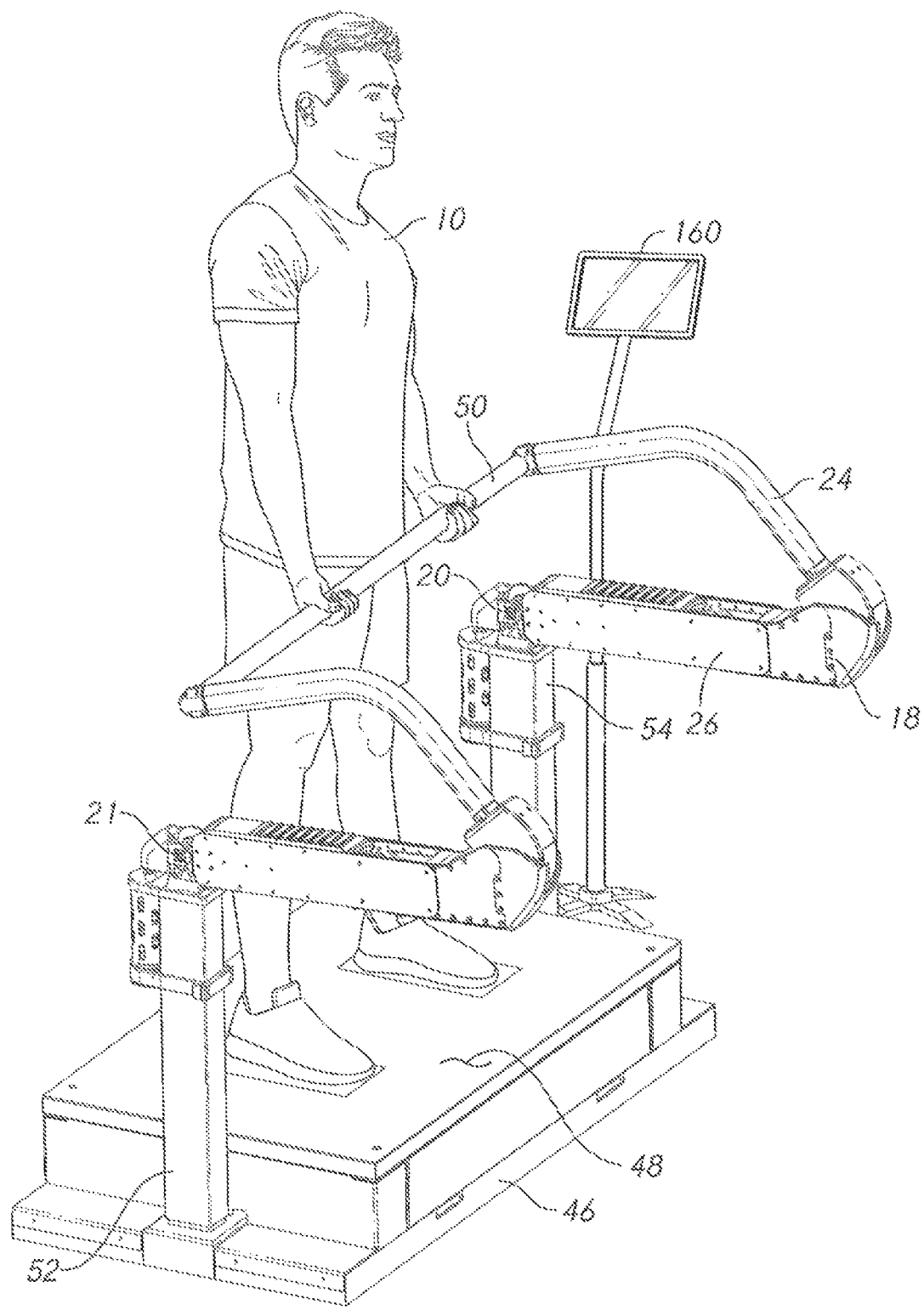
FIG. 1 is a perspective view, showing an embodiment of the inventive exercise device and a user.

REFERENCE NUMERALS IN THE DRAWINGS 10 user
18 left/third pivot joint
20 left/second pivot joint
21 right/second pivot joint
24 left/upper link
26 left/lower link
46 base
50 bar
52 right column
54 left column
56 left/end effector point
58 left/actuator housing
60 dogleg
62 right/second pivot joint
63 right/second pivot joint
64 right/lower link
66 right/third pivot joint
68 right/upper link
70 right/end effector point
72 right/first pivot joint
73 right/first pivot joint axis 74 right/column cap
76 right/carrier
78 ball-and-socket joint
80 cable
82 guide roller
84 cam sheave
85 cable attachment point
86 fairlead roller
88 spring housing
90 spring
92 spring plate
94 right/inner column
96 flex conduit
98 bench
100 right/slide joint axis
102 left/slide joint axis
104 right/extended column
106 left/extended column
108 right/force plate
110 left/force plate
112 right/traveling mount
114 left/traveling mount
116 cable connection
120 arm
122 center of gravity
124 cam
126 spring
128 bar axis
130 load cell
132 load cell
134 load cell
136 load cell
138 instantaneous center of pressure
140 printed reference
142 stability polygon
144 load cell
146 load cell
148 load cell
150 load cell
151 left stability polygon
152 right stability polygon
154 left center of pressure
156 right center of pressure
158 control system
160 touchscreen display

DETAILED DESCRIPTION OF THE INVENTION

FIG. 1 depicts user 10 employing a preferred embodiment of the inventive exercise device. The reader will note that the inventive device includes many of the same components on its left side and its right side, and in fact many embodiments are symmetric with the exception of some control and monitoring features. A convention will be used to describe the symmetric components. The component name will be preceded by "left/" or "right/" to specify the side of the device on which the component resides. The user should bear in mid that the left and right version of a component will generally be identical.

Base 46 provides a foundation for the device and preferably houses some of the components needed. Right/column 52 and left/column 54 extend upward from the base. Two links are pivotally connected to each column. For example, left/lower link 26 is pivotally connected to the top of left column 54 (In the preferred embodiments this pivotal connection is complex and will be described in more detail subsequently). Left/upper link 24 is pivotally connected to left/lower link 26 by left/third pivot joint 18. The same structure of links is provided for the right side.

Bar 50 links the upper extremes of the left and right upper links. In the preferred embodiments, a powered actuator is configured to apply a controlled torque between each upper link and lower link. For example, a powered actuator provides a controlled torque across left/third pivot joint 18.

Figure 2:
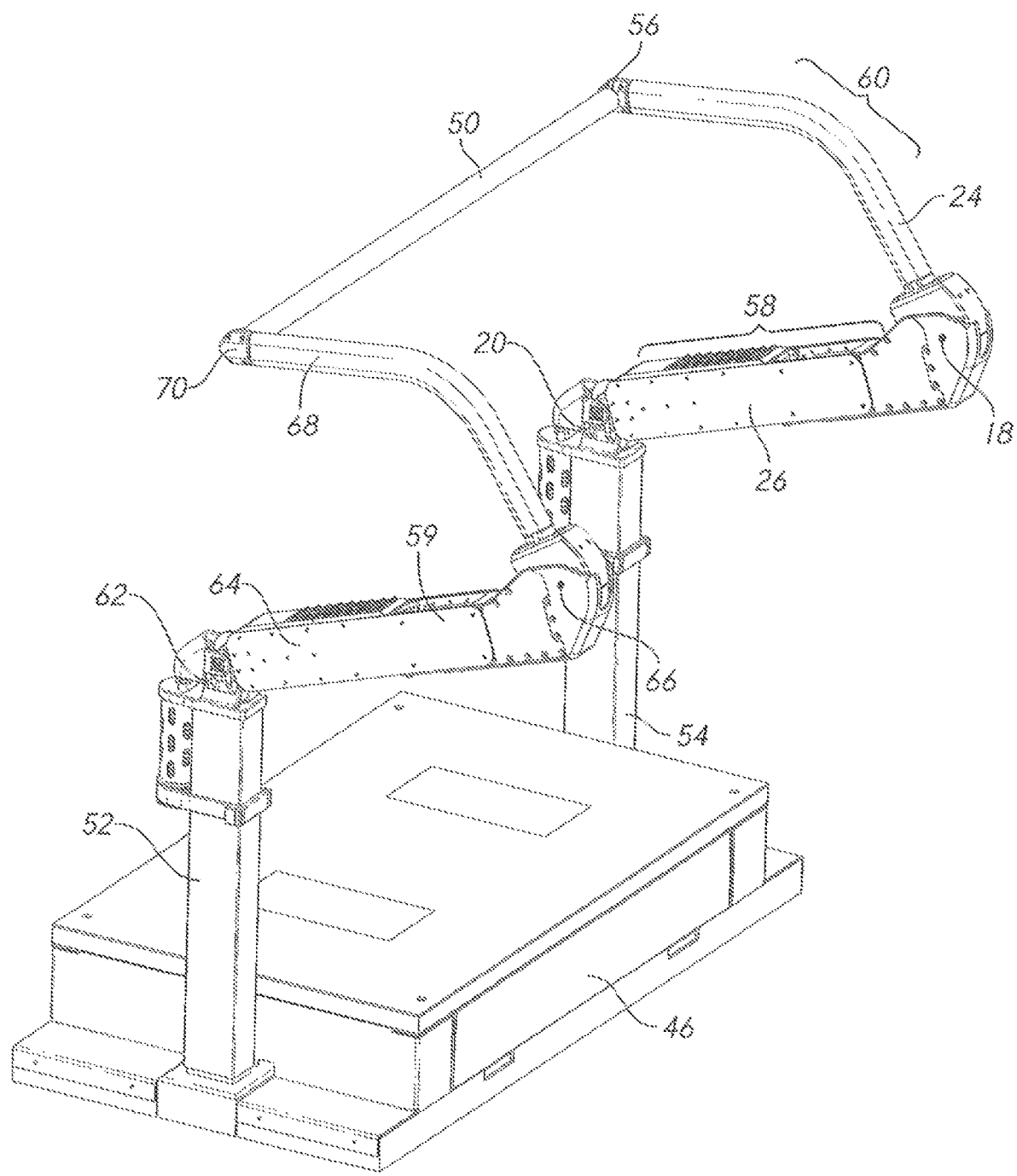
FIG. 2 is a perspective view, showing the embodiment of FIG. 1 from another vantage point.

FIG. 2 provides a perspective view of the embodiment of FIG. 1 without the user. The reader will note that right/lower link 64 is pivotally connected to the top of right/column 52. Right/upper link 68 is pivotally connected to right/lower link 64 by right/third pivot joint 66. In this example, the actuators are contained in the lower links (This need not always be the case). For example, left/actuator housing 58 forms part of left/lower link 26. Right/actuator housing 59 forms part of right/lower link 64.

Left/end effector point 56 lies at the upper extreme of left/upper link 24. Right/end effector point 70 lies at the upper extreme of right/upper link 68. The actuators in this example are electrical actuators that apply a controlled torque across the pivot joint connecting each upper link to each lower link. As one example, the actuators may be a linkage actuator such as described in U.S. patent application Ser. No. 15/237,793. U.S. patent application Ser. No. 15/237,793 is hereby incorporated by reference. As those skilled in the art will recognize, the application of a torque across left/third pivot joint 18 will result in a force tending to urge left/end effector point 56 away from the top of the left column or toward the top of the left column. This is the basic operating principle of the device.

Figure 3:
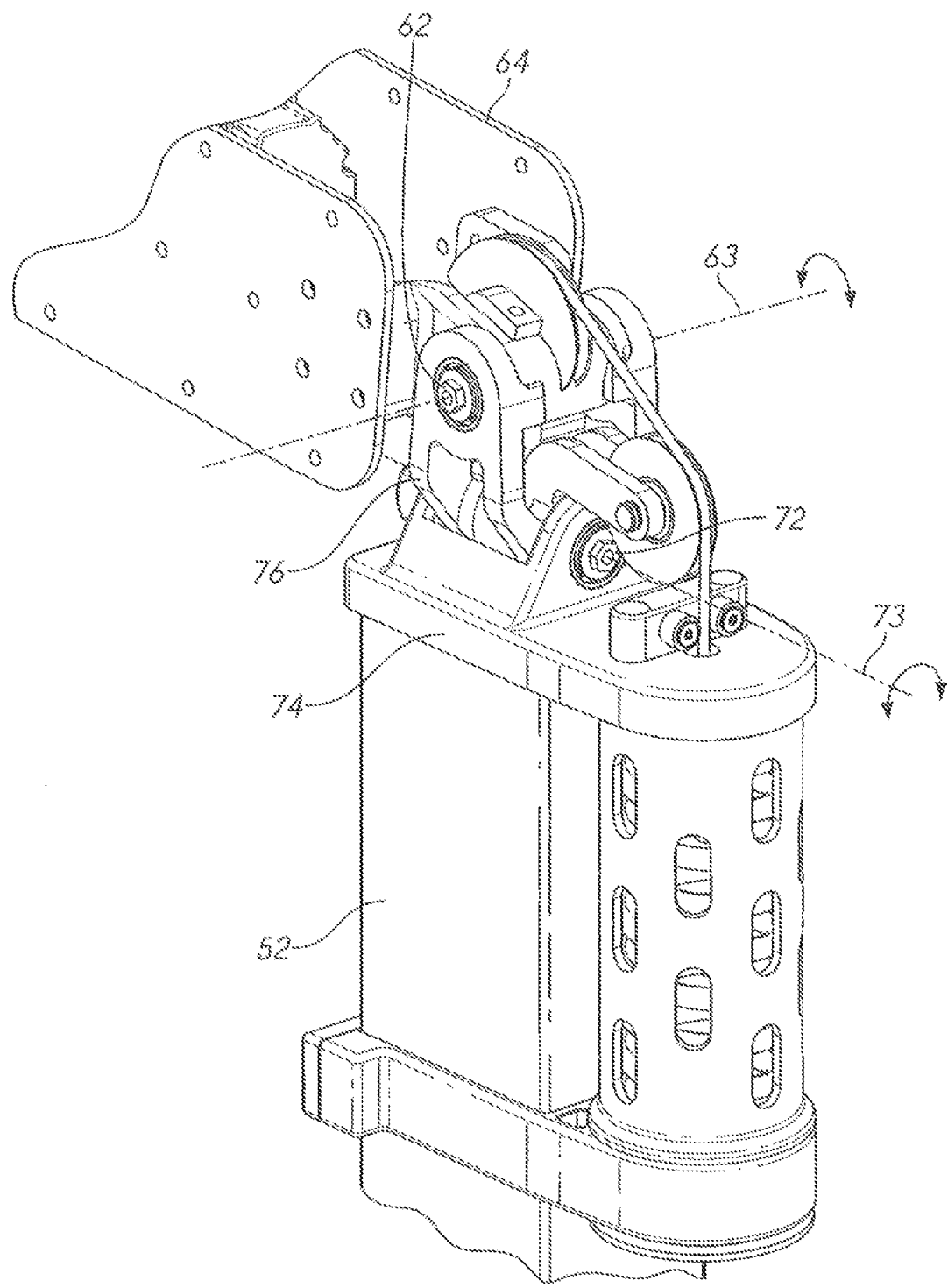
FIG. 3 is a detailed perspective view, showing an embodiment in which two pivoting joints connect the lower links to the tops of the support columns.

The inventive device is preferably provided with additional degrees of freedom—which will now be explained in detail. FIG. 3 provides an enlarged view of the top of right/column 52. Right/column cap 74 is secured to the top of the column. Right/first pivot joint 72 pivotally connects right/carrier 76 to right/column cap 74 as shown. Right/second pivot joint 62 pivotally connects right/lower link 64 to right/carrier 76.

The two pivot joints shown are orthogonal. Those skilled in the art will realize that a universal joint is thereby formed (using the convention previously defined this universal joint will be referred to as a right/lower universal joint and the identical structure mounted atop the left/column in this embodiment will be referred to as the left/lower universal joint). Right/first pivot joint 72 allows right/carrier 76 to pivot about right/first pivot joint axis 73 with respect to right/column cap 74 (as indicated by the first reciprocating arrows shown in the view). Right/second pivot joint 62 allows right/lower link 64 to pivot about right/second pivot joint axis 63 with respect to right/carrier 76 (as indicated by the second reciprocating arrows shown in the view).

Figure 4:
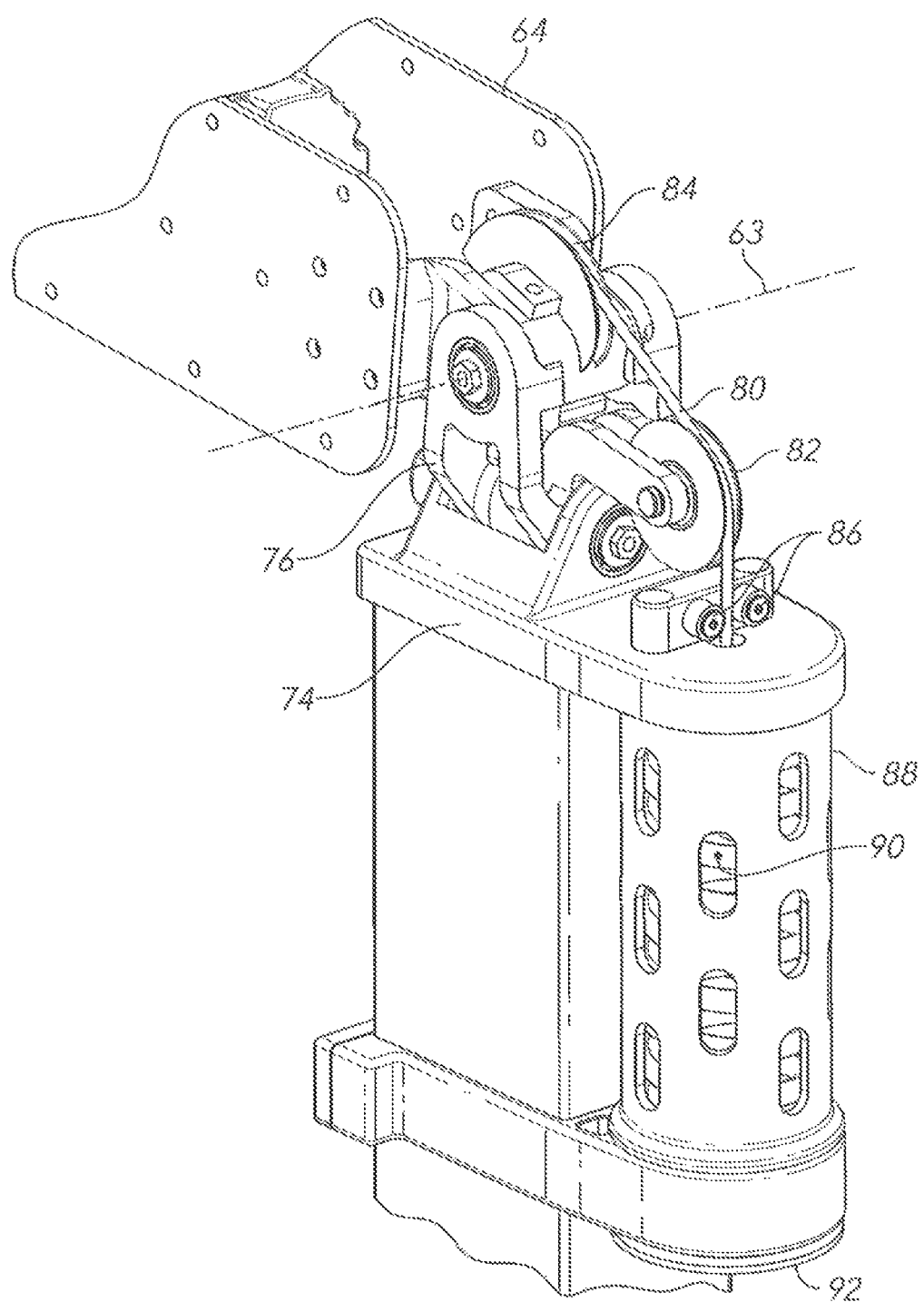
FIG. 4 is a detailed perspective view, showing the rotation axes for the depiction of FIG. 3.

FIG. 4 shows some additional details concerning the same components. It is preferable to provide a "counterweight" mechanism so that the static weight of the lower links, upper links, and bar are counterbalanced irrespective of their position. FIG. 4 illustrates one embodiment for such a mechanism. Cam sheave 84 is fixedly attached to right/lower link 64 so that it moves in unison with the right/lower link. Cable 80 passes through a groove in the outer perimeter of cam sheave 84 and is connected to cam sheave 84. The cable then passes around guide sheave 82 and through fairlead rollers 86. The cable then descends down and through spring housing 88. The lower portion of the cable is connected to spring plate 92, which is positioned to press upward against compression spring 90.

When right/loser link 64 pivots downward about right/second pivot joint axis 63, spring plate 92 moves upward and the compression placed on spring 90 is increased. Thus, the mechanism shown tends to counterbalance the weight of right/lower link 64 (and its connected upper link etc.). The reader will recall that the right/lower link can pivot about both pivotal connections depicted in FIG. 4.

Figure 5:
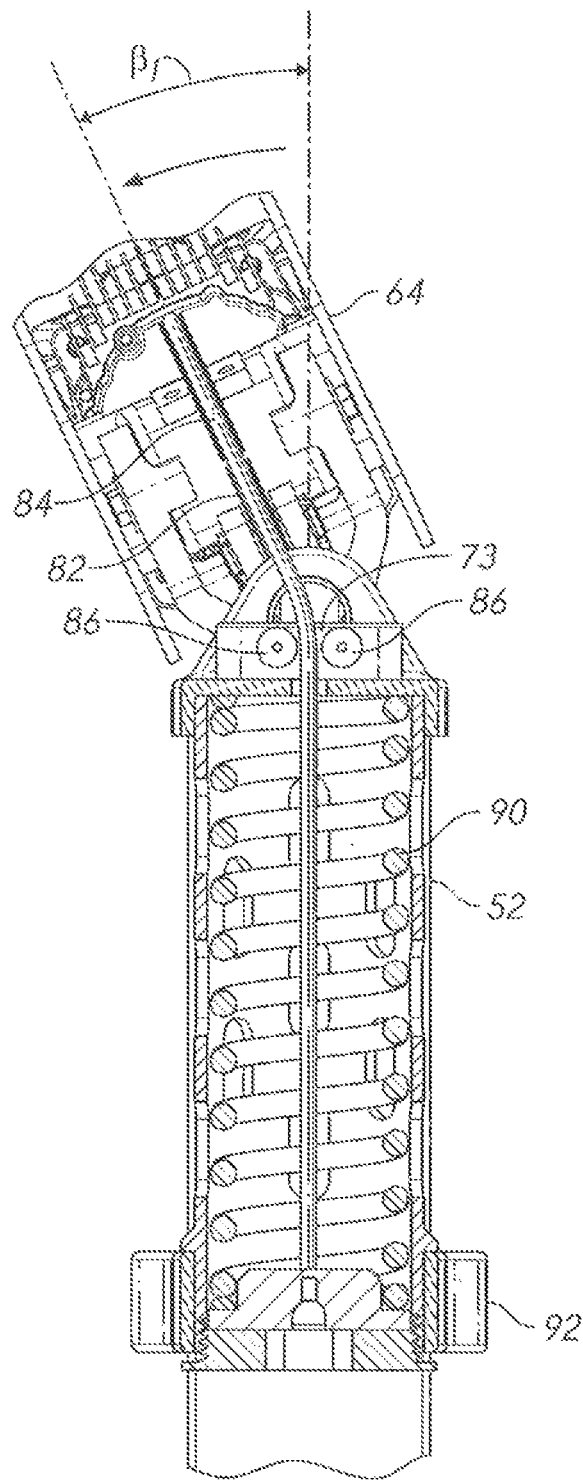
FIG. 5 is a rear elevation view, showing the operation of the pivoting joints.

Fairlead rollers 86 are provided to center the cable in the middle of spring 90 despite the variations in the position of right/lower link 64. FIG. 5 shows a rear elevation view of the same mechanism. The reader will note that right/lower link 64 has been pivoted laterally way from the vertical axis by an angle $\beta_1$. Fair lead rollers 86 center the cable despite the pivoted state.

Figure 6:
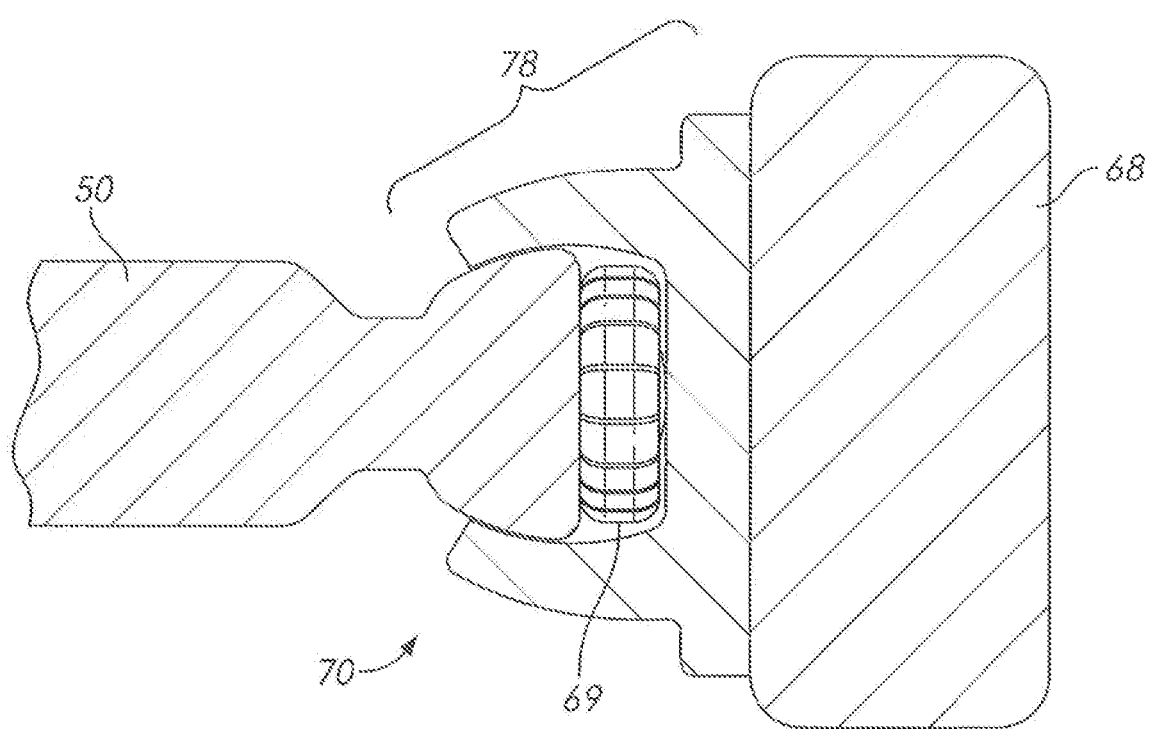
FIG. 6 is a sectional elevation view, showing a ball-and-socket joint that is used in some embodiments to connect the bar to the upper links.
Figure 7:
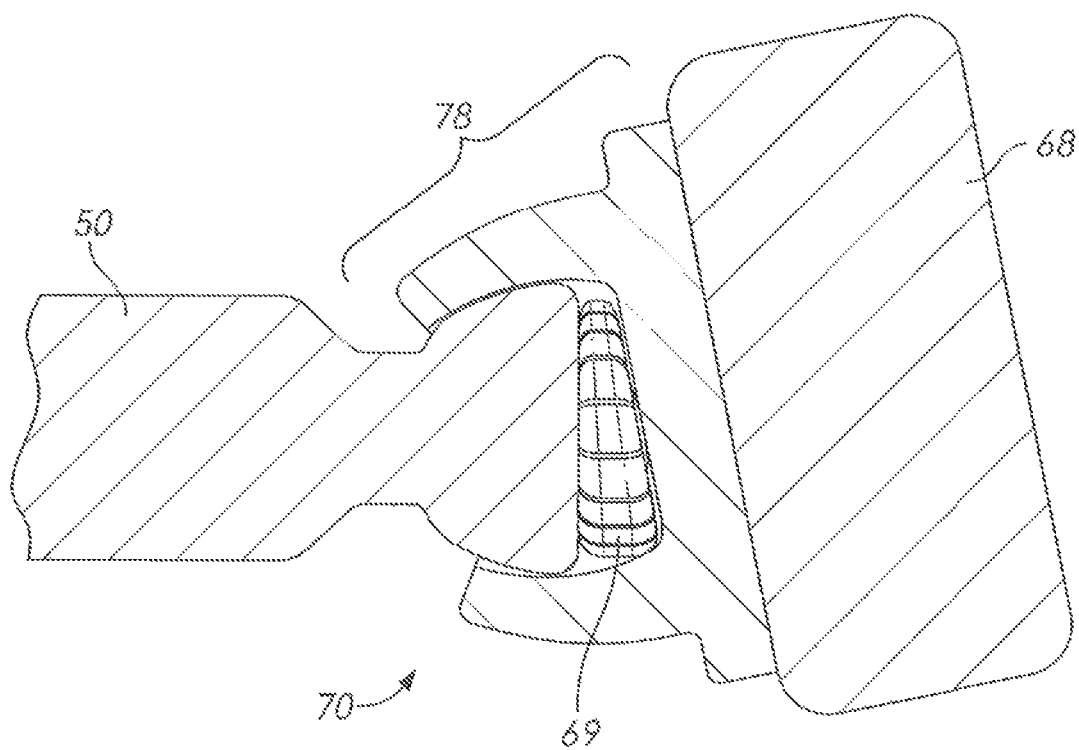
FIG. 7 is a sectional elevation view, showing the ball-and-socket joint of FIG. 6 in a pivoted state.

In order to accommodate the ability of the lower links to pivot laterally (as shown in FIG. 5), an additional degree of freedom is needed for the connection between bar 50 and the upper links. FIGS. 6 and 7 show a preferred embodiment for this connection. In FIG. 6, the reader will note the presence of ball-and-socket joint 78 linking bar 50 to right/upper link 68 (in the region of right/end effector point 70). Compressible cushion 69 is provided inside this joint to eliminate slack. The same type of joint is located on the opposite end of bar 50. FIG. 7 shows the same ball-and-socket joint in a deflected state. Cushion 69 has compressed on one side to allow bar 50 to pivot with respect to right/upper link 68.

The ball-and-socket joint depicted is a type of universal joint. The joint connecting the right end of the bar to the right/upper link will therefore be referred to as the right/upper universal joint. The joint connecting the left end of the bar to the left/upper link will be referred to as the left/upper universal joint.

Figure 8:
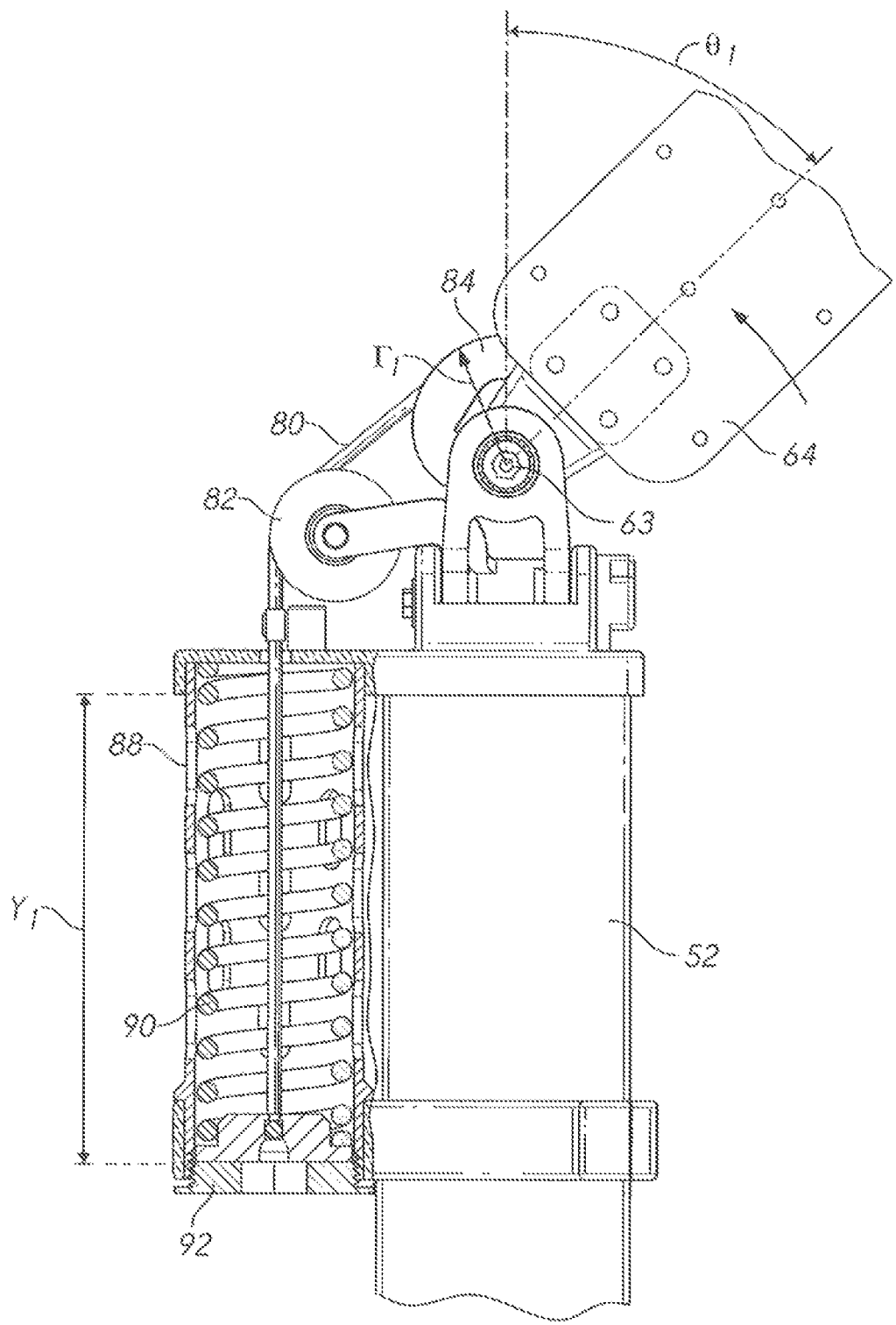
FIG. 8 is a side elevation view, showing the operation of the counterbalance mechanism in the pivoting joints.
Figure 9:
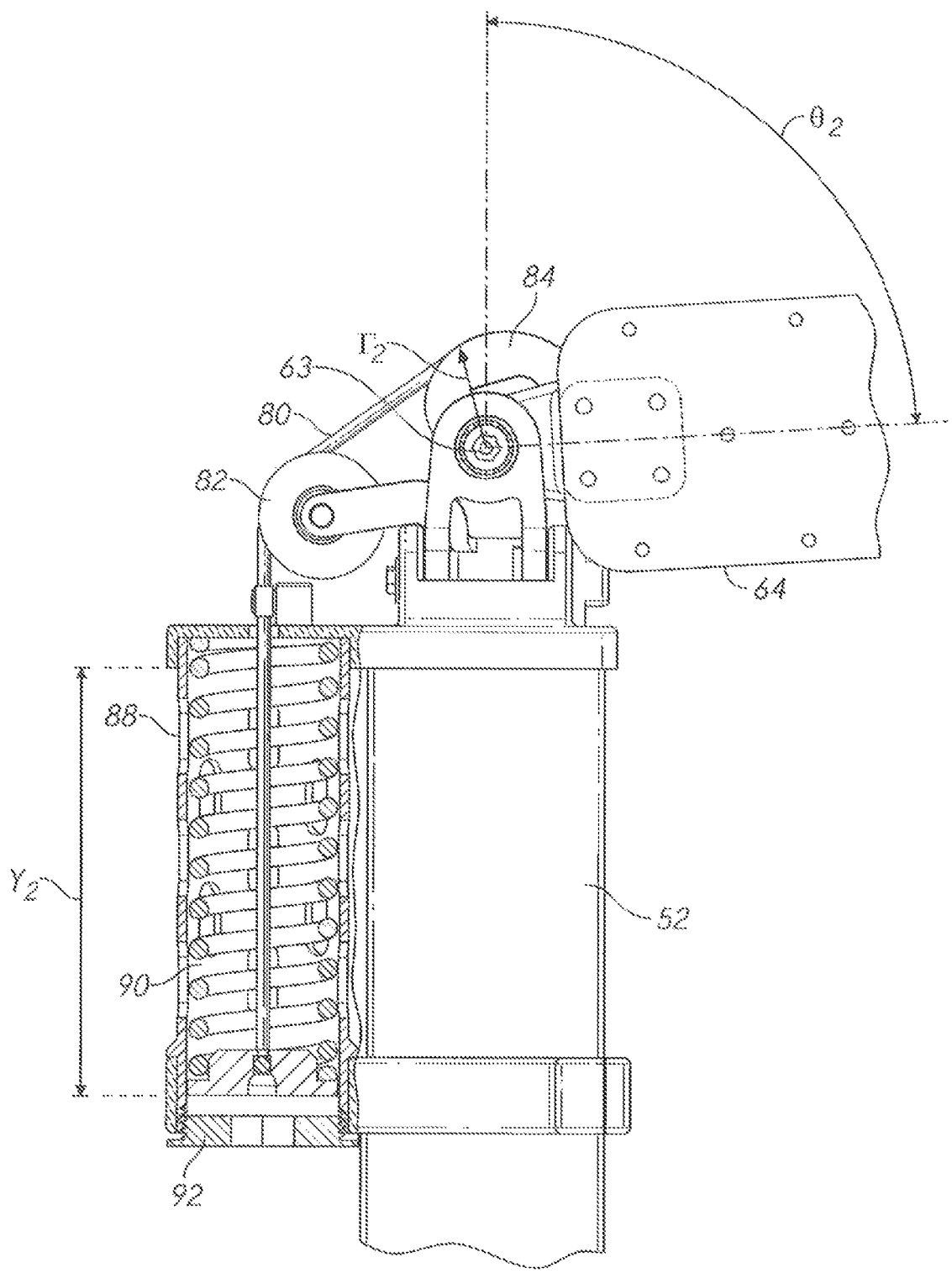
FIG. 9 is a side elevation view, showing the operation of the counterbalance mechanism in the pivoting joints.
Figure 10:
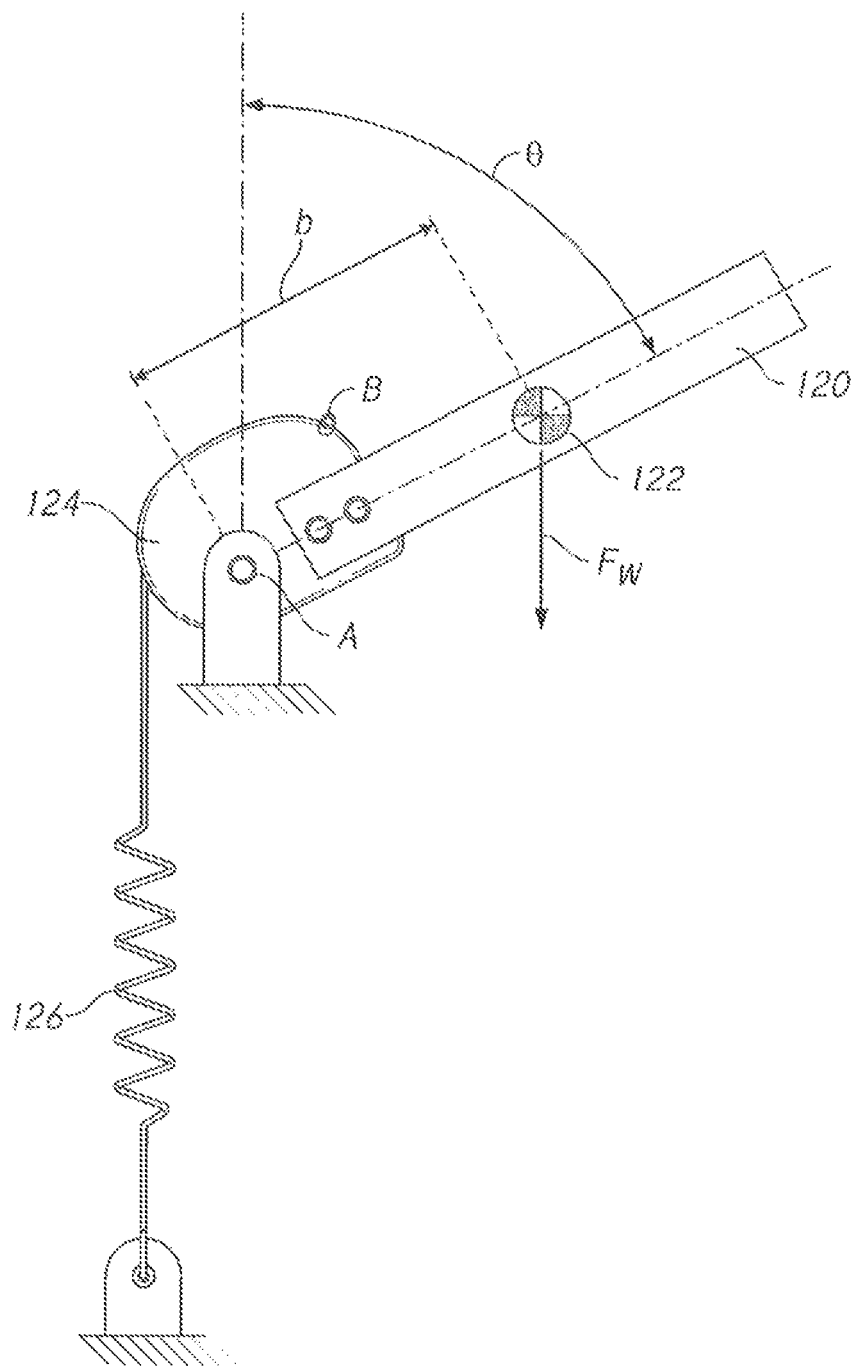
FIG. 10 is a conceptual view illustrating the operation of the counterbalance mechanism.

FIGS. 8-10 show additional details of a preferred embodiment of a counterbalancing system. A cam (cam sheave 84) is used so that the compression on the spring can be made non-linear and thereby can be made to apply an effective counterbalance for the different angular positions of the lower and upper links. The general principles of the mechanism will be explained initially and then some more advanced design constraints will be explained.

FIG. 8 shows the inventive exercise device with right/lower link 64 in a moderately raised position. The centerline of right/lower link 64 is resting at an angle $\theta$ measured in the clockwise direction from the vertical axis depicted. As explained previously, cable 80 is attached to spring plate 92. From that point it passes around guide sheave 82 and cam sheave 84 before connecting to the cam sheave at cable attachment point 85. Cam sheave 84 is rigidly connected to right/lower link 64 so that it pivots in unison with the right/lower link. Guide sheave 82 pivots freely. Radius r is the instantaneous distance between right/second pivot joint axis 63 and the point where the cable first makes contact with cam sheave 84. This radius is variable. As the reader will observe, the radius decreases as the angle $\theta$ increases.

Another parameter is the level of compression of compression spring 90. This is indicated by the distance y. In FIG. 8, the distance $y_1$ corresponds to the radius $r_1$ and the angle $\theta_1$. In FIG. 9, the angle has increased to $\theta_2$. The radius has decreased to $r_2$. The distance from the housing to spring plate 92 has decreased to $y_2$. In going from the position of FIG. 8 to the position of FIG. 9, the reader will appreciate that the compression of spring 90 has increased and that the tension on cable 80 has also therefore increased. However, the radius of the cable's contact with cam sheave 84 has decreased.

The objective of the counterbalance design is to equalize the torques about right/second pivot joint axis 63. A clockwise torque is produced by the weight of right lower link 64 (and its other connected components). An anticlockwise torque is produced by spring 90—acting through the cable connected to cam sheave 84. It is possible to configure the spring constant (by selecting the right spring wire size and pitch) and cam sheave profile so that the torque about right/second pivot joint axis 63 is balanced (or nearly balanced) for any angular position of right/lower link 64.

FIG. 10 shows a schematic depiction of the forces and torques involved. Cam 124 pivots about a fixed point A. Arm 120 is rigidly connected to cam 124. The arm has a center of gravity 122. The weight of the arm can be considered a vertical force passing through the center of gravity as shown. The center of gravity lies a distance b from the rotation point A.

A counterbalancing spring 126 is added. The lower end of the spring is connected to a fixed point. The upper end of the spring passes around the cam and attaches to the cam at a point B on the surface of the cam. It is possible to select a spring coefficient and a cam profile so that arm 120 is perfectly counterbalanced at any angular position $\theta$. Once these proper selections are made, a user can move arm 120 to any angular position and it will remain in that position. The arm freely moves but is properly counterbalanced at any position.

The selection of the correct spring constant and cam profile is beyond the scope of this disclosure. However the reader wishing to know more of the details of this process can refer to U.S. Pat. No. 4,768,762 which describes the process in detail. U.S. Pat. No. 4,768,762 is hereby incorporated by reference.

Figure 11:
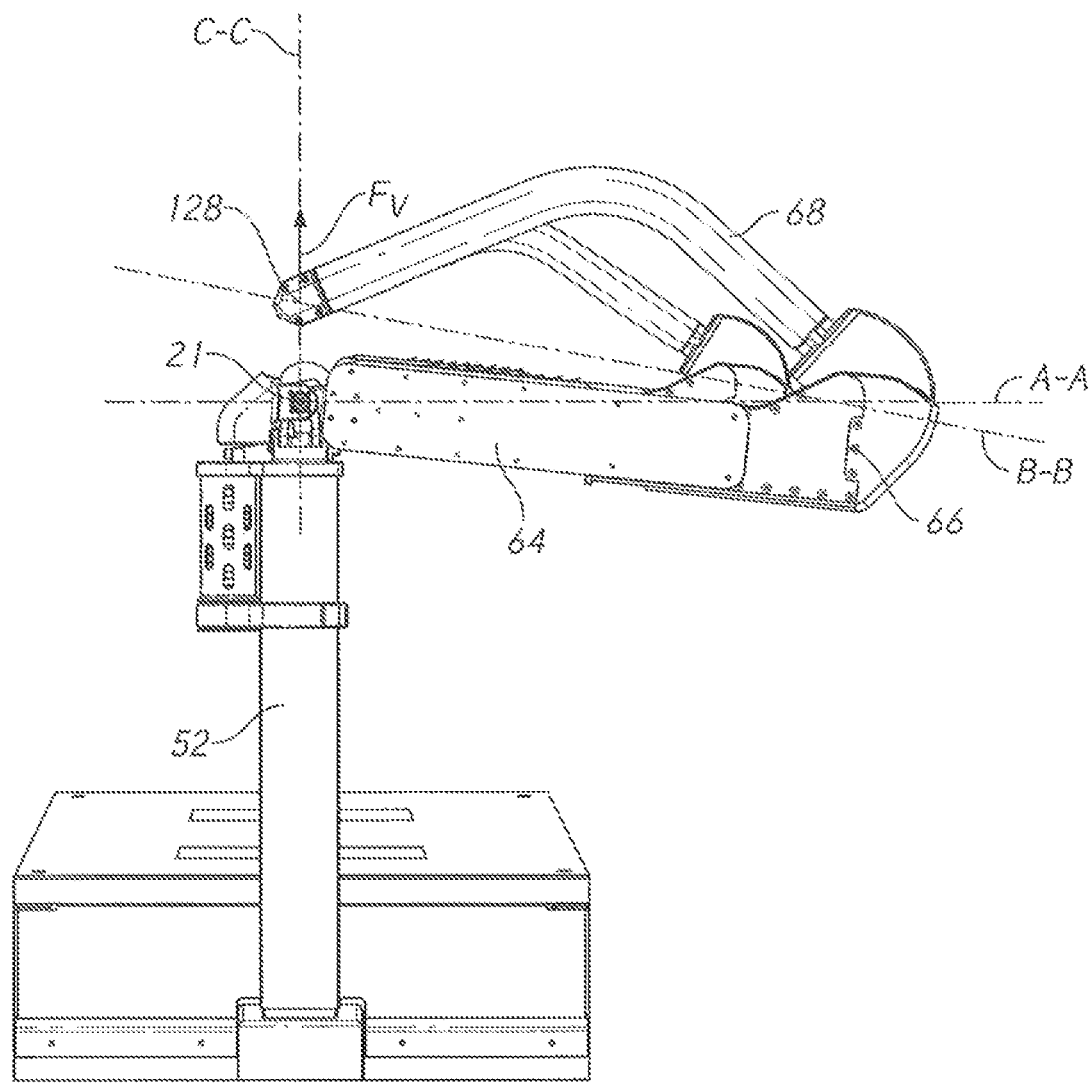
FIG. 11 is a perspective view, showing the operation of the invention.

FIG. 11 shows a side perspective view of a preferred embodiment of the present invention. The reader will note that the counterbalancing problem is not quite as simple as the mechanism shown in FIG. 10. In the present invention, the angular position of right/upper link 68 varies with respect to right/lower link 64. The center of gravity of the overall moving assembly therefore does not remain perfectly constant. In the nomenclature of FIG. 10, the distance b will vary somewhat for different angular positions of the upper and lower links. However, it does not vary a great deal. Thus, if the parameters for the counterbalancing mechanism shown in FIGS. 8 and 9 are selected to counterbalance an average position for the center of gravity they will provide effective (through somewhat imperfect) counterbalancing across the entire range of positions for the center of gravity.

Figure 12:
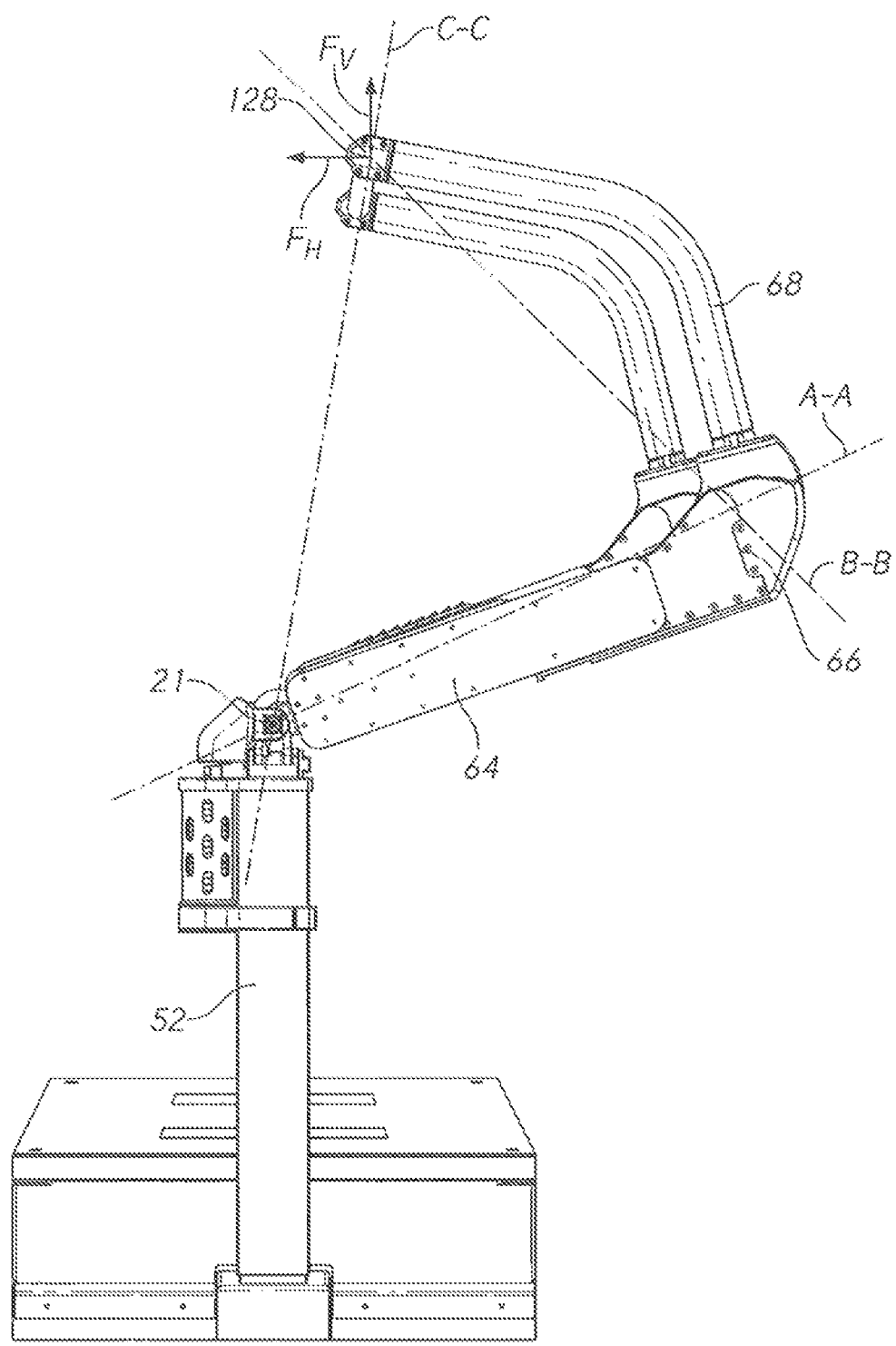
FIG. 12 is a perspective view, showing the operation of the invention.
Figure 13:
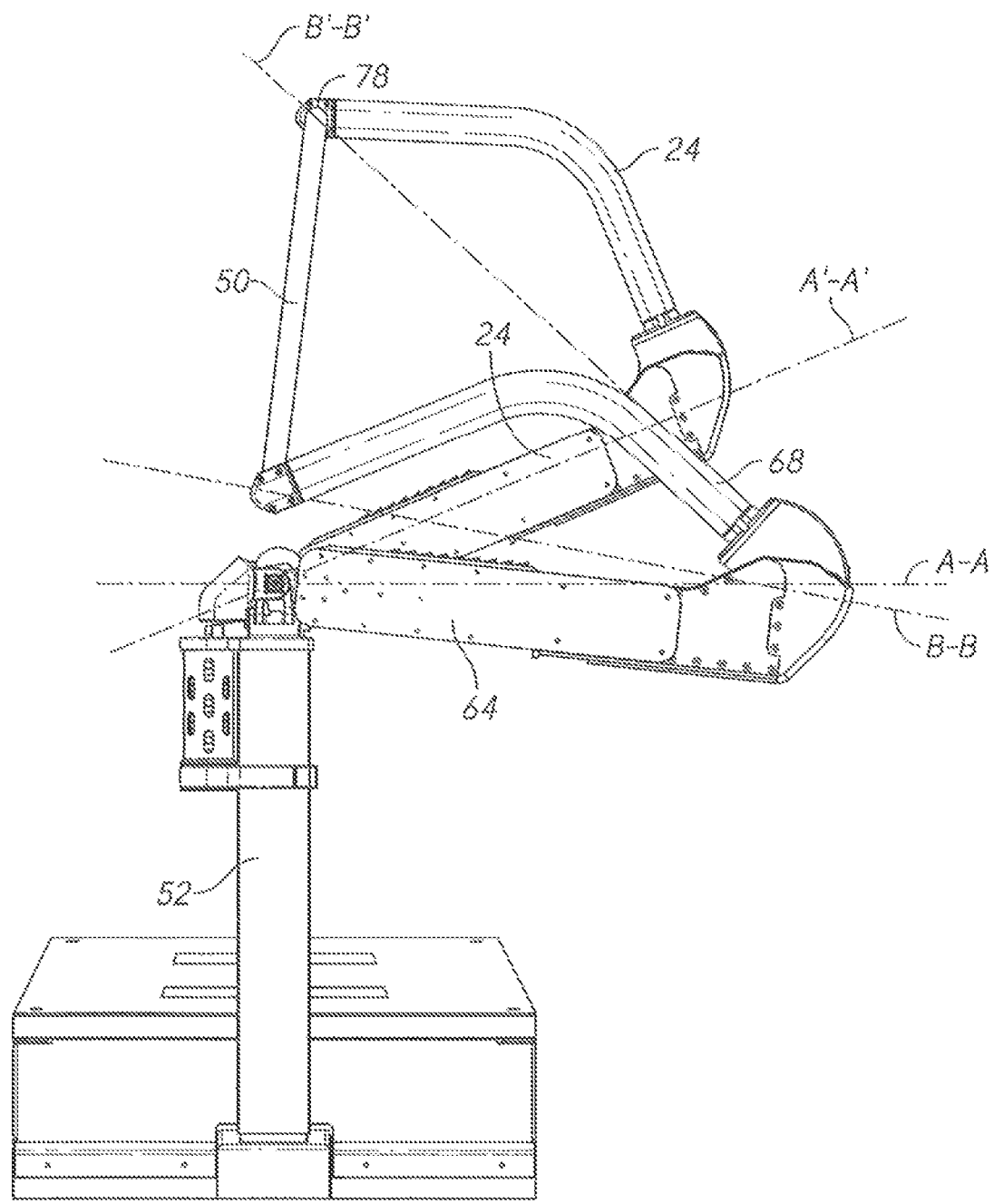
FIG. 13 is a perspective view, showing the operation of the invention.

FIGS. 11-13 serve to illustrate some of the operational principles of the preferred embodiments. FIG. 11 shows the invention with the lower links and upper links in the lowest position. Bar axis 128 runs through the center of bar 50. In the positions shown for the moving components the bar axis is perpendicular to the page. The user interacts with the device (in most configurations) by grasping the bar and exerting forces on the bar. Axis A-A runs from right/second pivot joint 21 through right/third pivot joint 66. Axis B-B runs from right/third pivot joint 66 through bar axis 128. Axis C-C runs from right/second pivot joint 21 through bar axis 128.

In this embodiment of the invention the actuators control torque (and possibly angular position) across the third pivot joints 18, 66. The actuator in right/lower link 64 applies torque across right/third pivot joint 66. In one exercise the user grasps the bar and pulls the bar upward—creating a vertical force $F_v$. The reader will observe how this force $F_v$ passes along the axis C-C. For this reason, the application of force by the user does not tend to pivot right/lower link 64 about the passive joint 21. Thus, controlling the torque about right/third pivot joint 66 is sufficient to counteract the force applied by the user (without having to power right/second pivot joint 21).

FIG. 12 shows the same embodiment with bar 50 raised to an elevated position. The reader will note that bar 50 has been allowed to move somewhat forward. In order to counteract the torque applied by the actuator across right/third pivot joint 66, the user must apply a force having a large vertical component $F_v$ and a small horizontal component $F_h$. In the position shown the axis C-C has tilted off the vertical and this requires the user to add the horizontal component to maintain a static balance where the links are not moving. This balance is quite similar to that required to keep a free weight steady. The user will instinctively move the bar rearward (to the left in the view) to null the horizontal component and make the balancing of the forces easier.

FIG. 13 provides a perspective view with the same vantage point as used in FIGS. 11 and 12. The reader will recall that bar 50 links the two sets of movable arms. Each side can be independently controlled, as this view illustrates. The axes A-A and B-B are in the same position as shown in FIG. 11. However, the corresponding axes for left/lower link 26 and left upper/link 24 (axes A'-A' and B'-B') are rotated significantly.

This position can be the result of different things. As one example, a control system can be set to apply constant torque across the right and left powered joints 18, 66 while allowing the angular position of these two joints to "float." If a user is much stronger on the left side than the right (common in rehabilitation exercises) then the left side of bar 50 may be propelled upward much faster than the right. The inventive embodiment of FIG. 13 can accommodate this condition, owing to the ball-and-socket joints 78 on each end of bar 50.

In order to accommodate the tilted configuration of the bar present in FIG. 13, the two lower links will need to tilt toward each other. This tilting is allowed via the first pivot joint axis on each side (see first pivot joint axis 73 in FIG. 3). Thus, the reader will understand that a user standing on the force plate can move the bar laterally and angularly (in addition to moving it up and down). The degrees of freedom provided in the invention allow for these complex motions.

Figure 14:
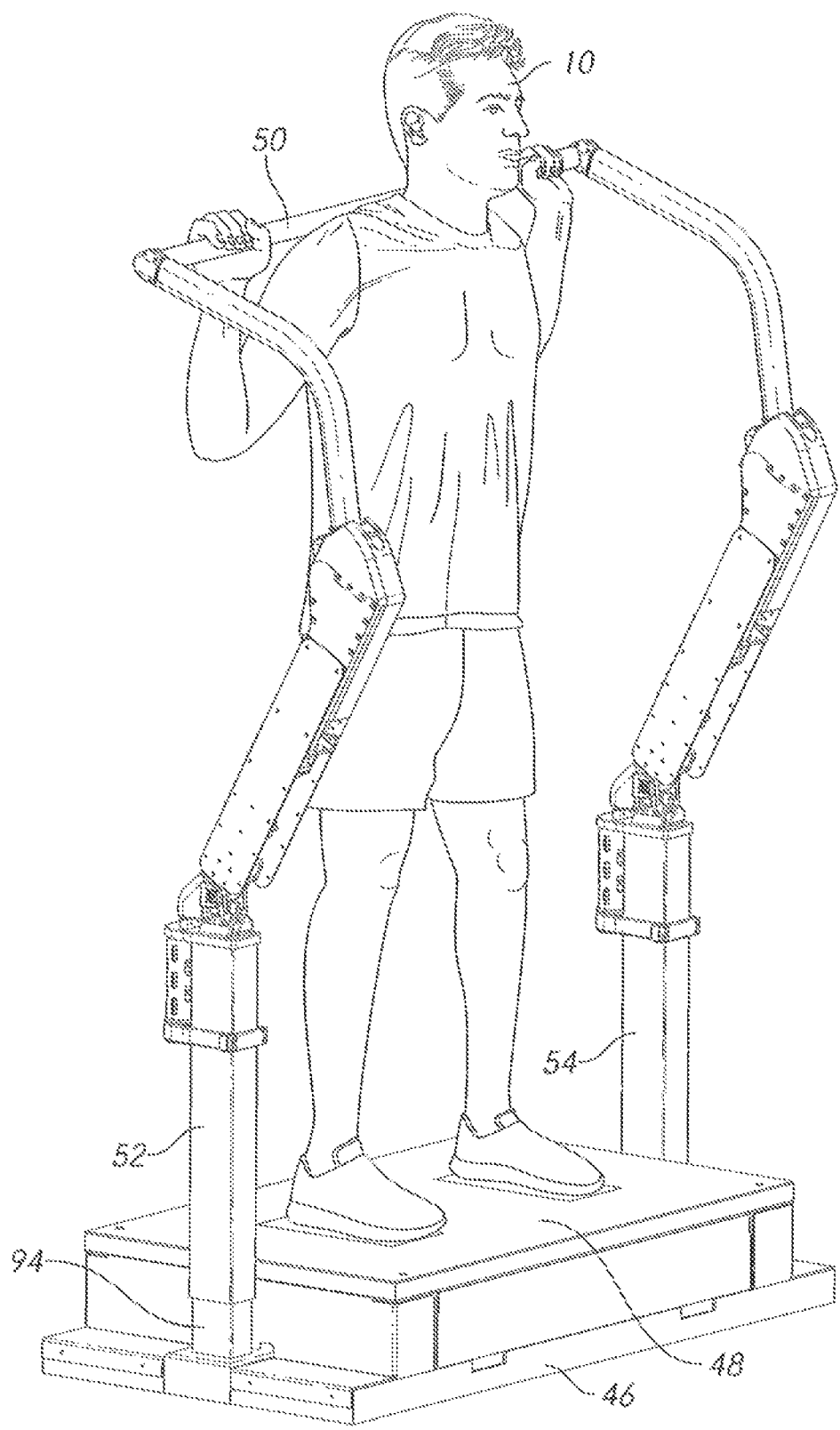
FIG. 14 is a perspective view, showing how the vertical position of the support columns can be altered to suit various exercises.
Figure 15:
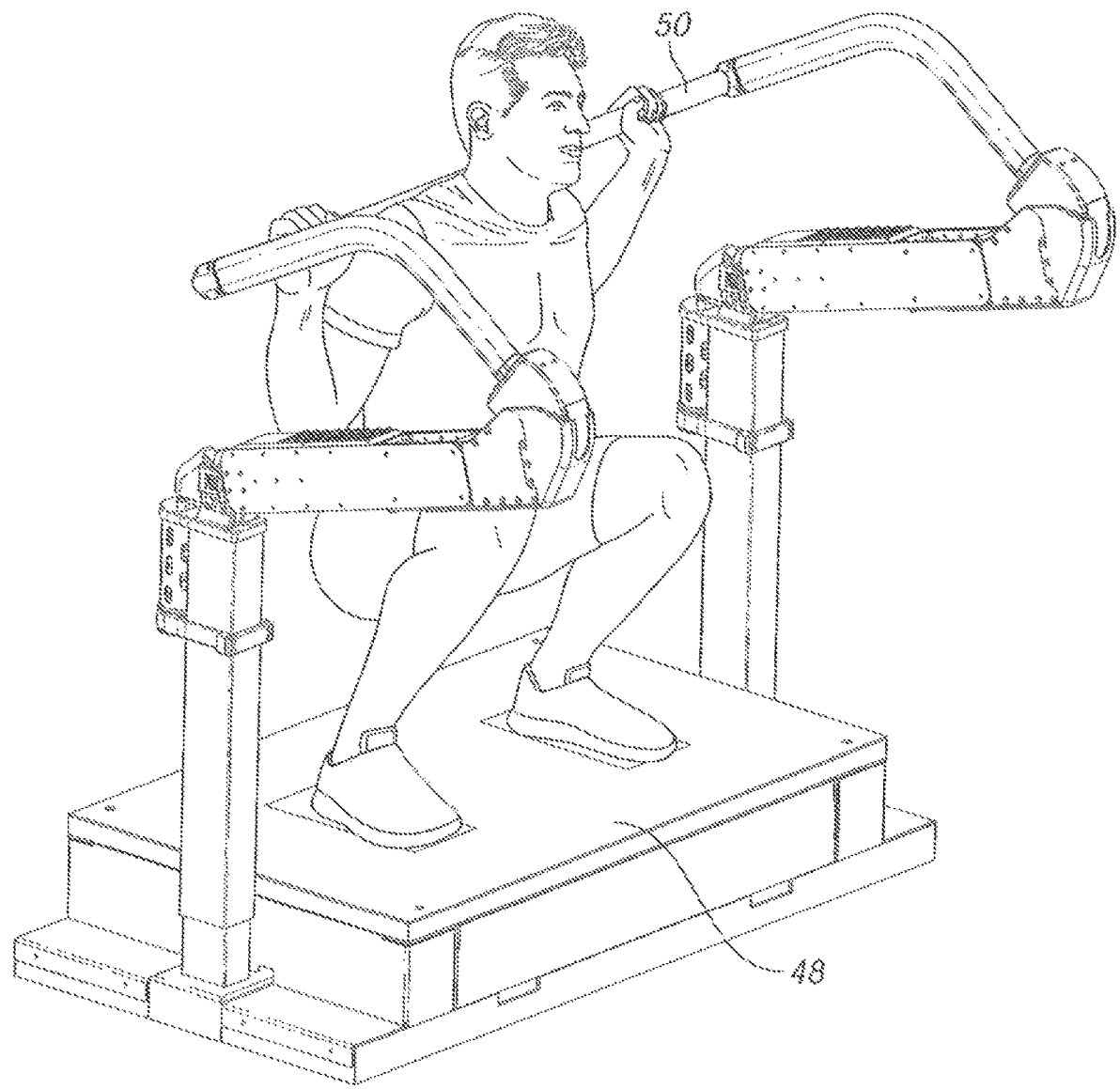
FIG. 15 is a perspective view, showing the configuration of FIG. 14 with a user in the low squat position.
Figure 16:
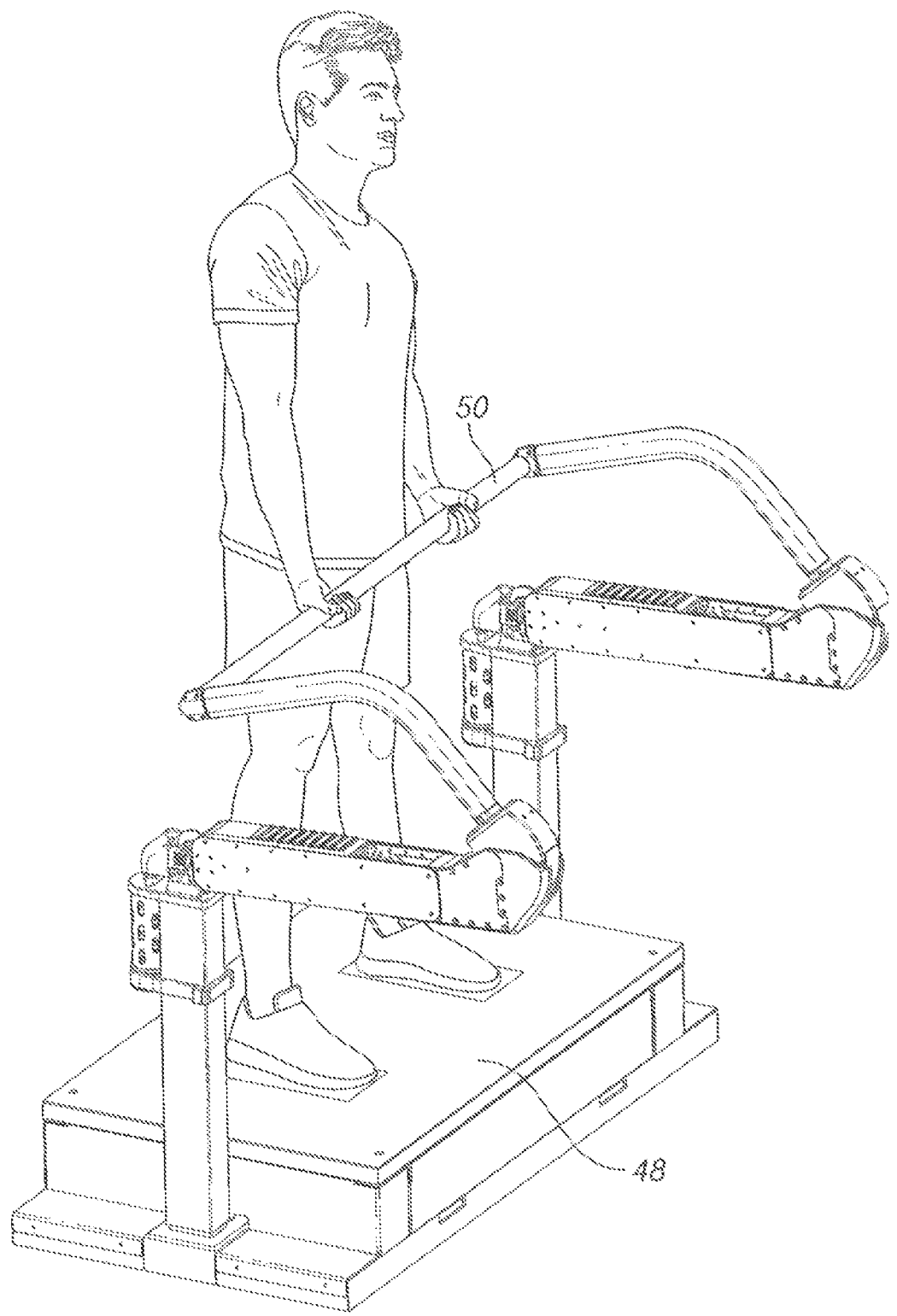
FIG. 16 is a perspective view, with the embodiment of FIG. 1 being configured for a curl exercise.

FIGS. 14-16 illustrate some exemplary exercises that can be performed using the invention. FIG. 14 shows the starting position for a squat exercise. Bar 50 has been placed across the user's shoulders in a horizontal orientation. The reader will note that the lower and upper links on both sides have been raised significantly. It is desirable to accommodate a wide variety of users and the squat exercise serves to illustrate the range of heights needed.

A tall user (2.0 meters) will require a starting bar height of about 1.7 meters. A small user will require a starting bar height of only 1.0 meters. A wide range can be accommodated via the pivoting of the upper link with respect to the lower link and the pivoting of the lower link with respect to the column. However, it is preferable to provide some adjustment in the height of the columns themselves.

Still looking at FIG. 14, right column 52 telescopically slides over right inner column 94. Likewise, left column 54 telescopically slides over a corresponding left inner column. In the example shown an electrically-actuated screw drive is used to raise and lower the columns 52, 54. The height of the columns can be adjusted independently, but usually they will be configured to move in unison. As shown, the columns 52, 54 have been raised so that the starting position of bar 50 is realized without unduly extending the upper and lower links.

FIG. 15 shows the low position of the squat exercise commencing with FIG. 14. As is known to those skilled in the art, a squat cycle requires the user to lift the bar from the position shown in FIG. 15 up to the position shown in FIG. 14. During this motion the control system of the present invention controls the torque across third pivot joints 18, 66. The control system is preferably a closed-loop system receiving angular position, angular velocity, and torque information for each joint.

The control system can be used to mimic the forces of a free weight. Consider two simple examples for a free weight: In the first example the user moves the bar very slowly upward. In this instance the dynamic forces are negligible and the user simply counters gravity. In the second example the user moves the bar very quickly. In this second instance the dynamic forces at the bottom of the upward motion will be quite significant, and the force required will be much greater. At the top of the motion the upward velocity of the free weight is decreasing and momentum will cause the overall force to be less than the force caused by gravity.

The control system can be configured to mimic these two scenarios and everything in between. For the first instance the control system varies the torque across third pivot joints 18, 66 so that the downward force on the bar remains constant. In the second example the control system adds additional variation in the torque across the pivot joints to mimic the dynamic forces of a free weight.

FIG. 16 shows the invention configured for use in a prior art curl exercise. Bar 50 occupies the starting position in this view. The user lifts the bar through an arc to perform the curl. The counterweight mechanism allows the starting position to be achieved without the exertion of significant force. The control system can be configured to allow passive manipulation to the desired start position. The user then provides a start command and the active control is initiated. The start command can be entered by a touch scree, a foot-activated button, a voice command system, or any other suitable method.

The simulation of free weight exercises is a significant feature of the invention, but the invention is by no means limited to these scenarios. In fact, a significant advantage of the invention is its ability to mimic free weights in some aspects while completely altering the force characteristics of free weights in others. As one example, it is often desirable to alter the lifting profile during the rehabilitation of a shoulder injury. A physical therapist in this instance wishes to have the patient's injured shoulder move through the range of motion of an overhead press exercise without loading the joint. If the patient's right shoulder is normal and the left shoulder is being rehabilitated, the invention can be set to apply weight-mimicking loads to the right shoulder and no loads to the left. The motion of the right upper and lower links can even be set to be the "master" and the motion of third pivot joint 18 (on the left side) can actually be driven to match the motion of third pivot joint 66 (on the right side). In this instance the left shoulder is actually assisted in maintaining the position of the left end of bar 50. In other words, the control system applies negative torque to the powered joint on the right side (which the user must counter) while applying positive torque to the powered joint on the left side to assist the user in raising the injured joint.

The control system can also be configured to apply forces in the following ways:

1. A changeable force that increases or decreases over different portions of the range of motion;

2. A pulsing force;

3. A free weight mimicking force that adds disturbing forces to challenge or test the user;

4. A changeable force that decreases over a particular portion of the range of motion in order to reduce the chance of exacerbating an existing injury.

Figure 17:
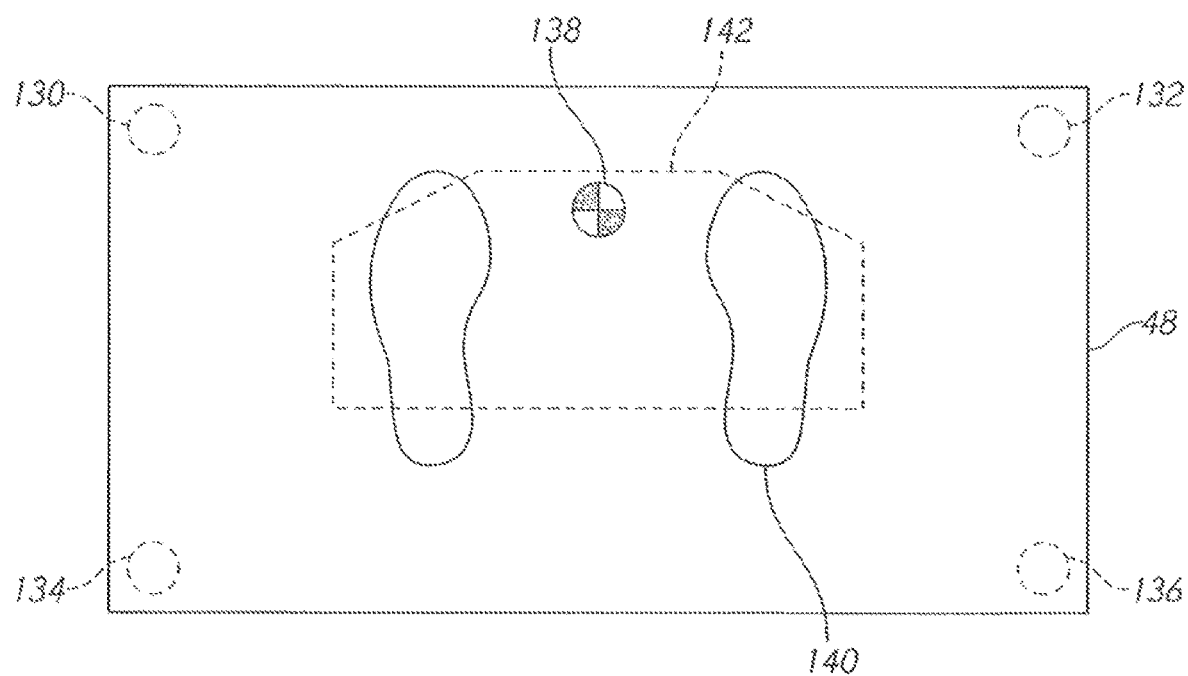
FIG. 17 is a plan view of the force plate, showing an exemplary stability polygon.

It is advantageous to supply the control system with reaction forces produced by the user's feet. Returning to FIG. 1, the reader will note the presence of force plate 48 on base 46. This force plate can be used to measure reaction forces. FIG. 17 shows a plan view of force plate 48. In the embodiment shown, load cells 130, 132, 134, 136 are placed on each corner. As those skilled in the art will now, a load cell generally includes a strain gage that is placed on a compression block. A monitoring system measures the electrical characteristics of the strain gage (often a variable voltage drop) and thereby determines the amount of force currently being applied to the load cell.

Using the force information from the four load cells, the control system can determine the reaction forces created by the use's feet on the force plate. Reaction forces will of course include the user's static weight. They will also include additional varying forces produced in response to the user exerting force on bar 50. The control system uses these reaction forces to compute an instantaneous center of pressure 138 for the user. A stability polygon 142 is defined within the software of the control system. The stability polygon is a geometric boundary that contains all the "safe" locations for instantaneous center of pressure 138. Printed references 140 are provided to give the user a good starting position for his or her feet. So long as the user's feet are near these printed references, stability polygon 142 provides a good definition of a balanced state. If the instantaneous center of pressure moves outside of stability polygon 142, then the user is off-balance. In this example the control system is programmed to remove all forces once an off-balance state is detected. Thus, even though the system can closely mimic the forces found with free weights, it can also instantly remove the forces if a problem is detected.

The control system can also be set to monitor the velocity of the instantaneous center of pressure. This can be important in detecting user imbalance. If the center of pressure is moving rapidly toward the edge of the stability polygon—even though it remains within the polygon—the control system can remove all loads.

Figure 18:
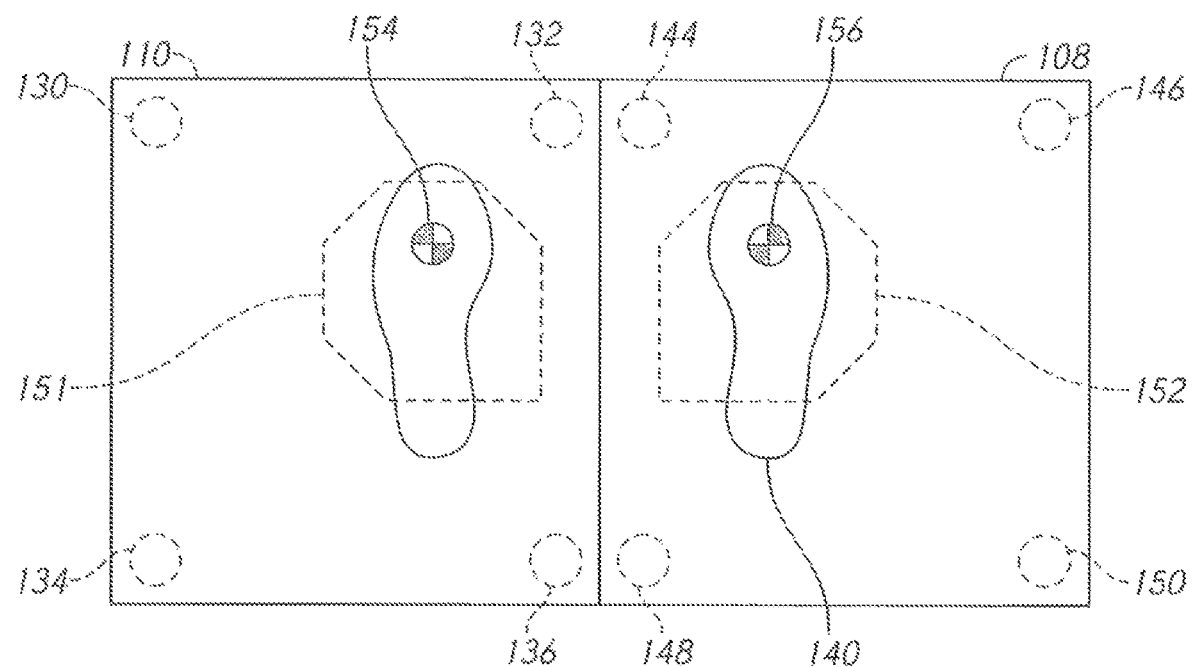
FIG. 18 is a plan view of a split force plate, showing an exemplary stability polygons.

FIG. 18 shows an additional embodiment in which the force plate is divided into two independently monitored force plates—right force plate 108 and left force plate 110. Left force plate 110 is equipped with four load cells 130, 132, 134, 136. Right force place 108 is also equipped with four load cells 144, 146, 148, 150. The split configuration allows the control system to calculate an instantaneous center of pressure 154, 156 for each foot. A stability polygon 151, 152 is also provided for each foot. Loss-of-balance detection is carried out for each foot individually, which can be helpful in cases of asymmetric strength and/or balance.

Figure 19:
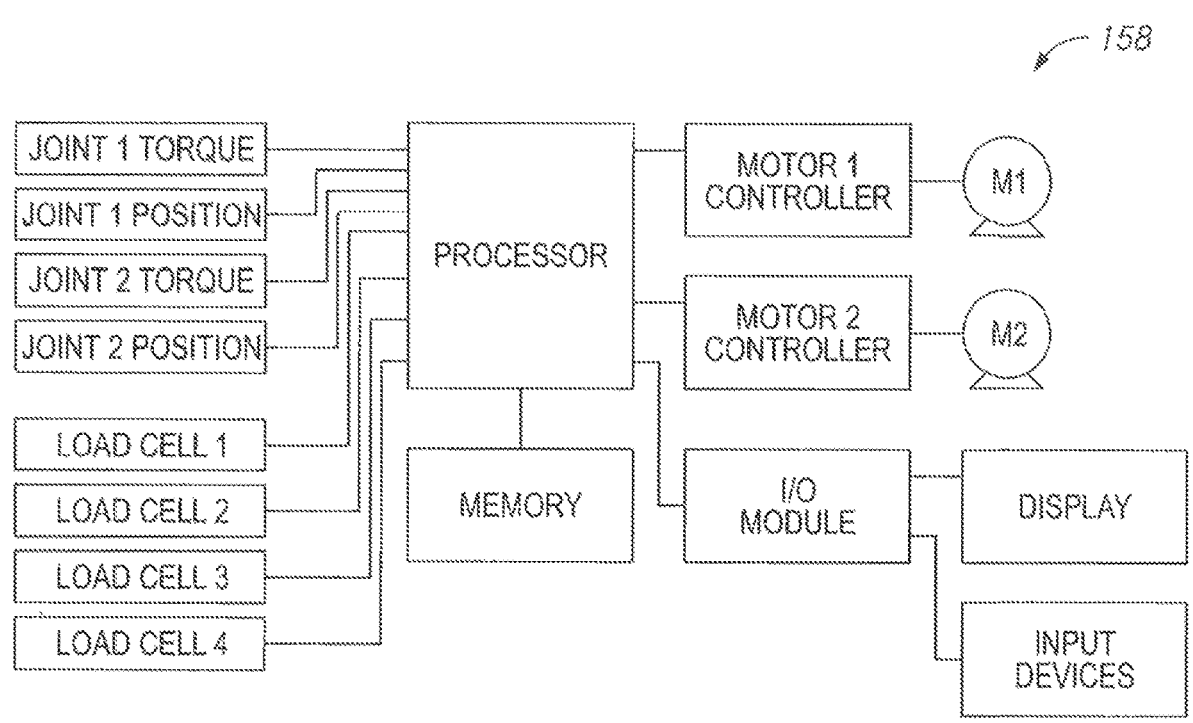
FIG. 19 is a schematic view depicting an exemplary control system that can be used with the present invention.

Many different control systems can be used in the present invention. FIG. 19 depicts an exemplary system. A processor runs control software. An associated memory is provided for storing the software and for storing the current state of the parameters used in the control routine. The primary outputs for the processor are the Motor Controllers and the I/O Module. Motor Controller 1 controls the motor applying torque across left/third pivot joint 18. Motor controller 2 controls the motor applying torque across right/third pivot joint 66. The I/O Module provides the graphical user interface that is preferably displayed on a touch screen (such as display 160 shown in FIG. 1). The I/O Module takes information from the processor and transforms it for display to the user. The I/O module also receives user inputs (in the form of a screen touch typically) and transforms these for use by the processor.

An important class of inputs for the processor are torque measurements across the powered joints and position measurement taken at the powered joints. The "Joint 1" measurements pertain to left/third pivot joint 18 while the "Joint 2" measurements pertain to right/third pivot joint 66. As those skilled in the art will know, the torque will often be calculated as a function of motor current. Joint position will often be measured by a rotary encoder. Both these values may be fed through the motor controller. Thus, there may be a single interface between each motor controller and the processor, rather than a separate interface for torque and position values.

An additional important class of inputs for the processor are the reaction forces measured by the load cells supporting the force plate or plates. Returning briefly to FIG. 17, the reader will recall that force plate 48 is supported by four load cells 130, 132, 134, 136. In the schematic diagram of FIG. 19, these four load cells are shown as additional inputs to the processor. The force measurements provided by the load cells are used by the processor to determine the instantaneous center of pressure and to perform the stability calculations.

Figure 20:
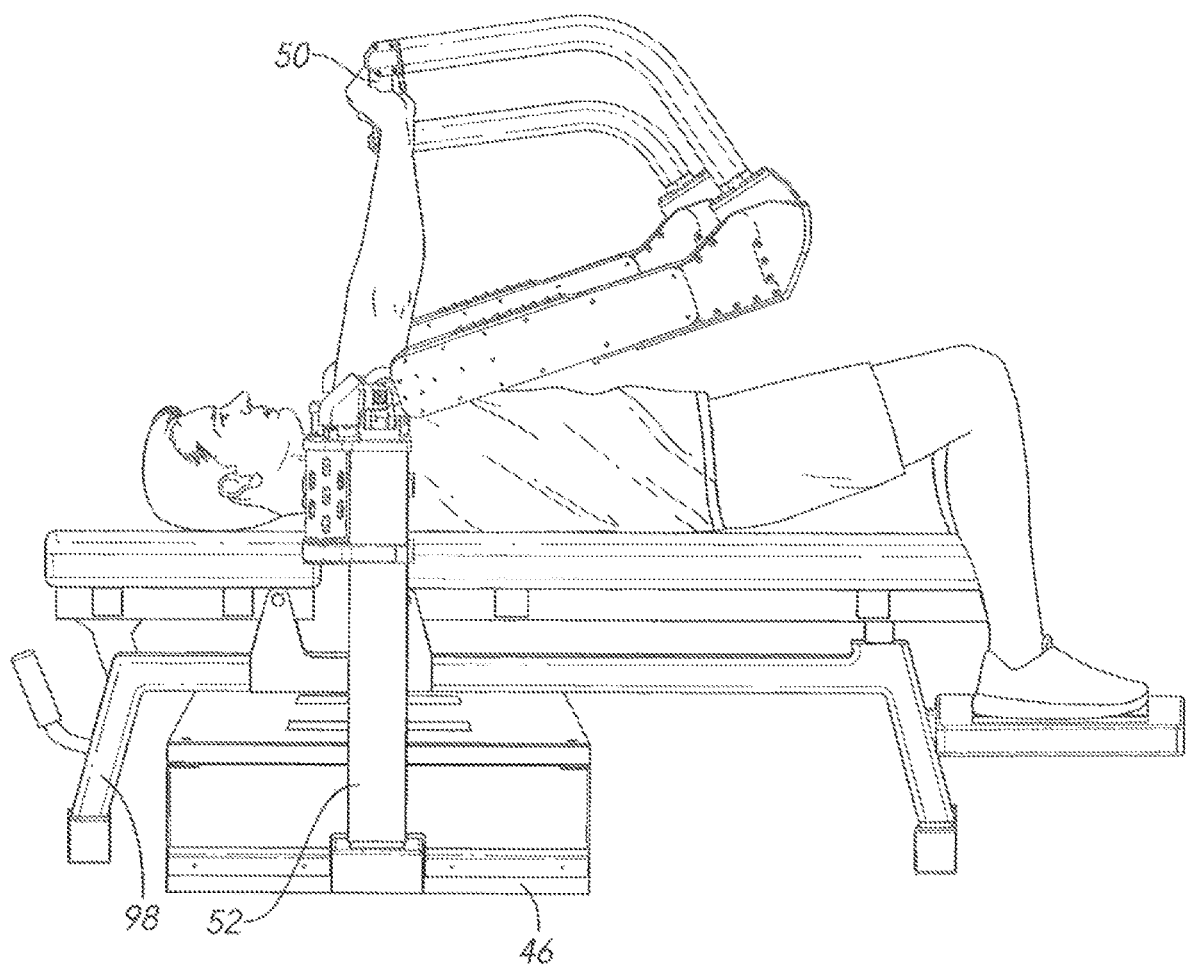
FIG. 20 is a side perspective view, with the embodiment of FIG. 1 being configured for a bench press exercise.

The control system can be configured to drive the use of the invention for many different types of exercises. FIG. 20 shows the invention being sued for a bench-press exercise. Bench 98 has been placed over base 46. The user lies on the bench and exerts force to move bar 50 upward. In this configuration the reaction force measurements from the force plate(s) are not available. Alternative safety features can be programmed into the control system for this situation. As an example, the user can "drop" the weight by ceasing all upward force on the bar. This will initially cause a rapid downward motion. The control system can be configured to interpret such a rapid downward motion as a "drop" and respond by removing the downward force and stabilizing the current position of the powered joints.

Figure 21:
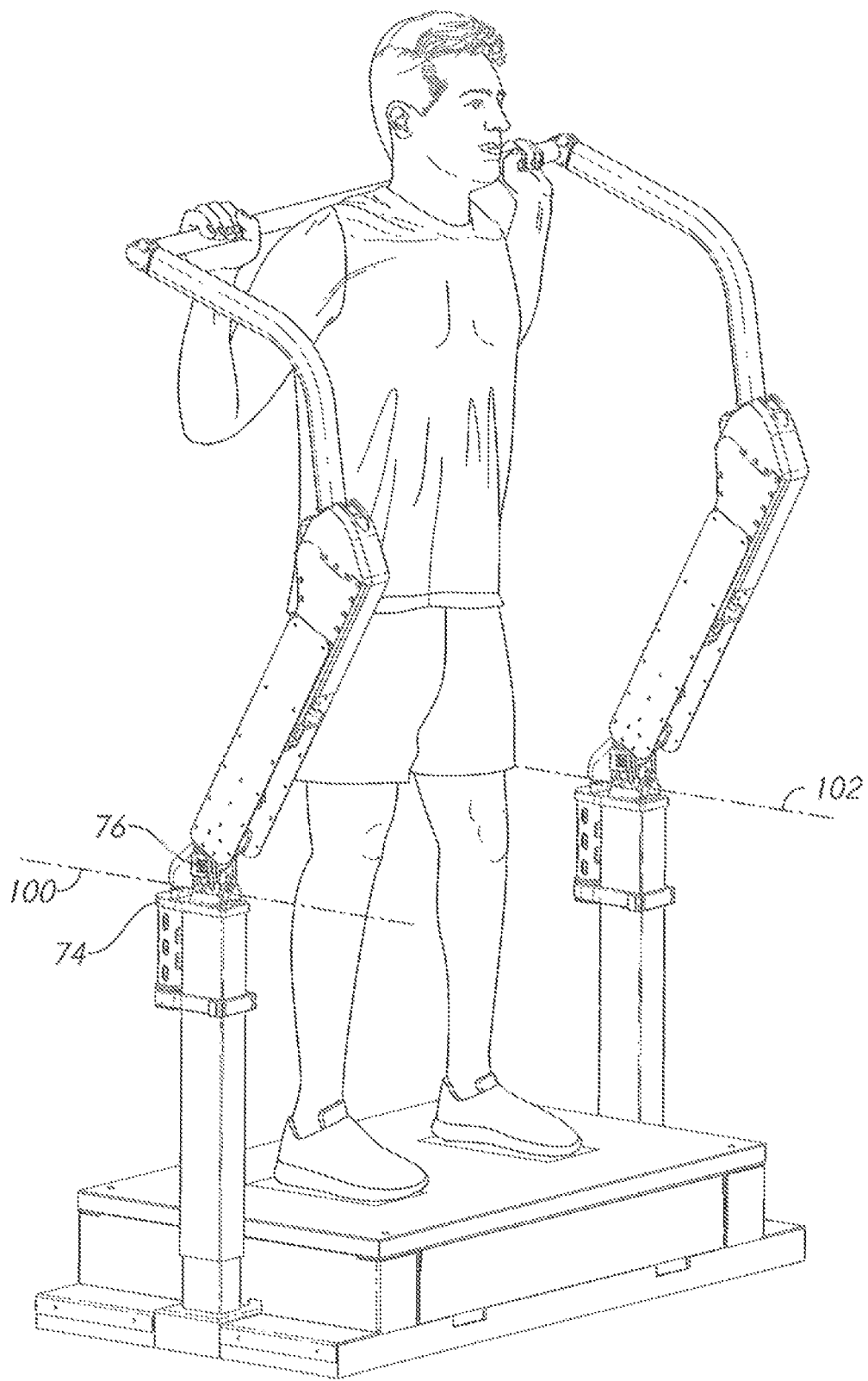
FIG. 21 is a perspective view, showing the addition of two linear joints to provide additional degrees of freedom.

Additional embodiments can provide additional degrees of freedom. FIG. 21 provides an example of a useful additional degree of freedom. In the embodiment shown a slide axis is added to the top of each column. A slide joint allows right carrier 76 to slide forward and backward with respect to right column cap 74. The sliding motion takes place along right slide joint axis 100. Right carrier 76 is able to slide along this axis. The lower link and upper link move along with the right carrier. A similar slide joint is added between the left carrier and left column cap. This second slide joint allows the left column cap to move with respect to the left column—along left slide joint axis 102. The presence of these two slide joints allows more fore-and-aft motion of the bar during exercises.

Figure 22:
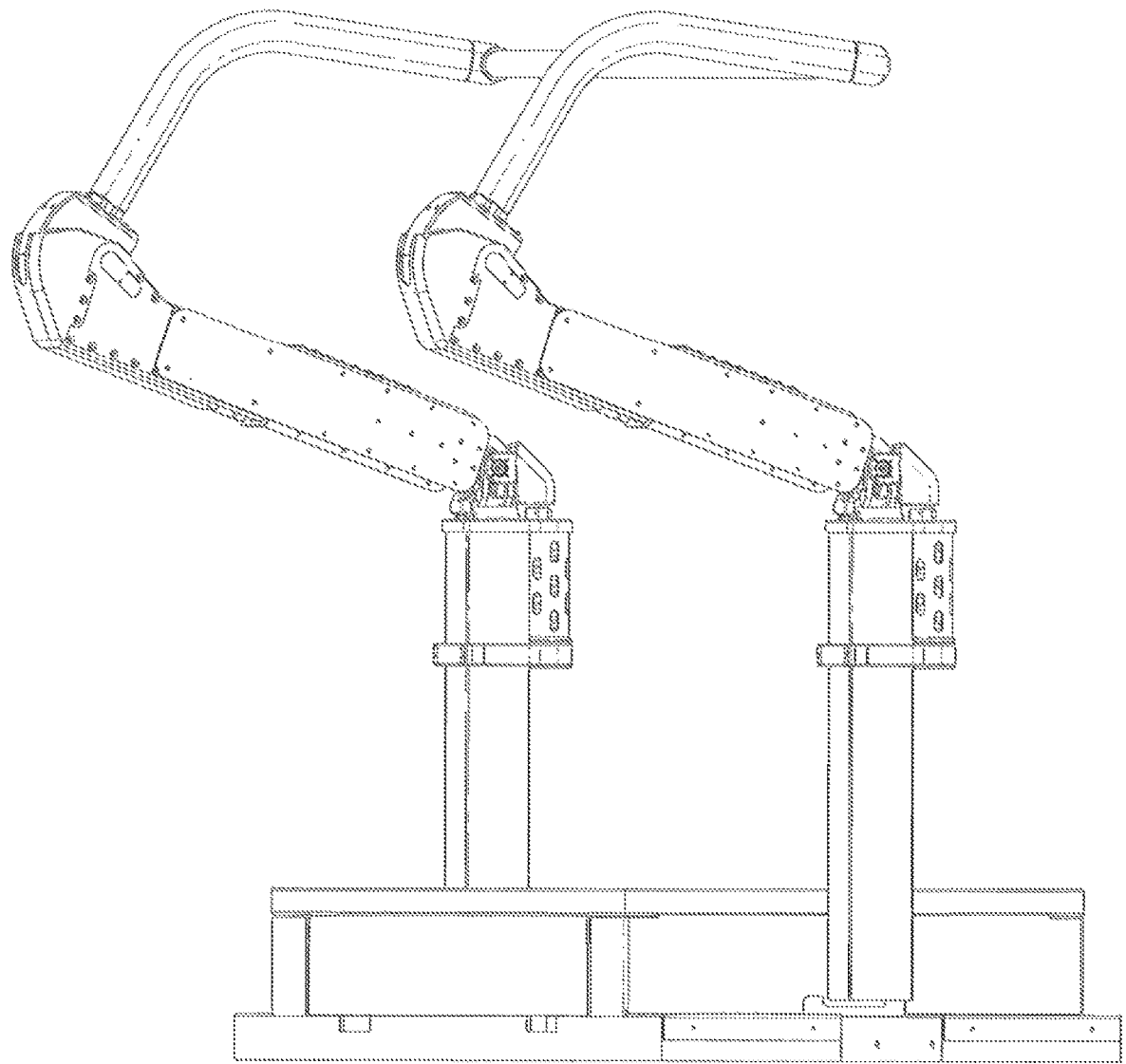
FIG. 22 is a perspective view, showing the embodiment of FIG. 1 from a different vantage point.

FIG. 22 provides a perspective view of a preferred embodiment with the upper links raised to an elevated position. The counterbalance mechanism present in the invention allows the machine to remain in this state even when the bar is not grasped by the user. The control system can be set to place the bar in such a state before an exercise starts. The user then grasps the bar and begins the exercise. The two carriers will tend to rotate somewhat about the right and left first pivot joints. This rotation will cause the bar to move laterally for a short distance. The user can easily center the bar at the start of the exercise.

Figure 23:
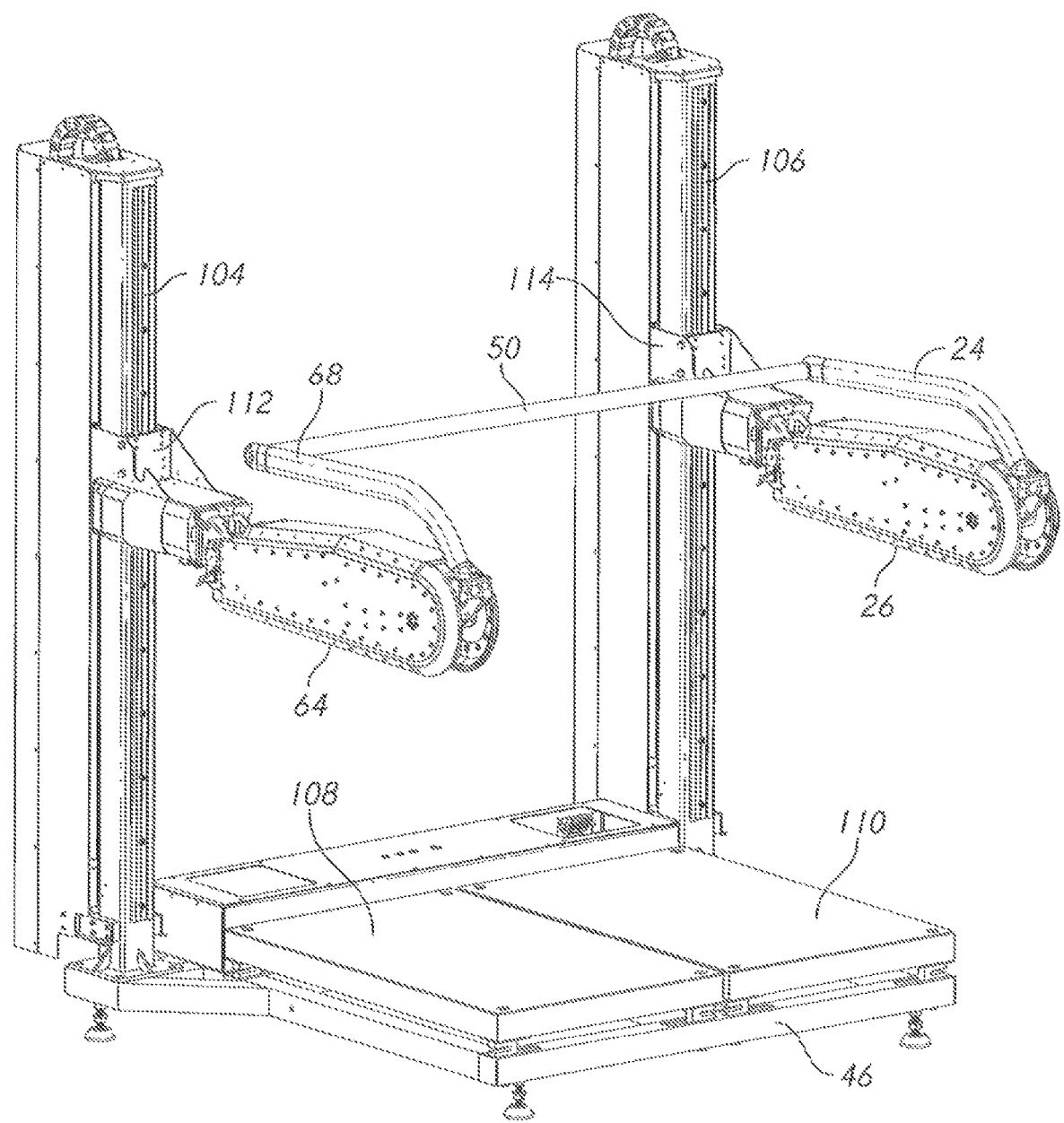
FIG. 23 is a perspective view, showing an additional embodiment of the inventive device that allows a greater range of vertical adjustment.
Figure 24:
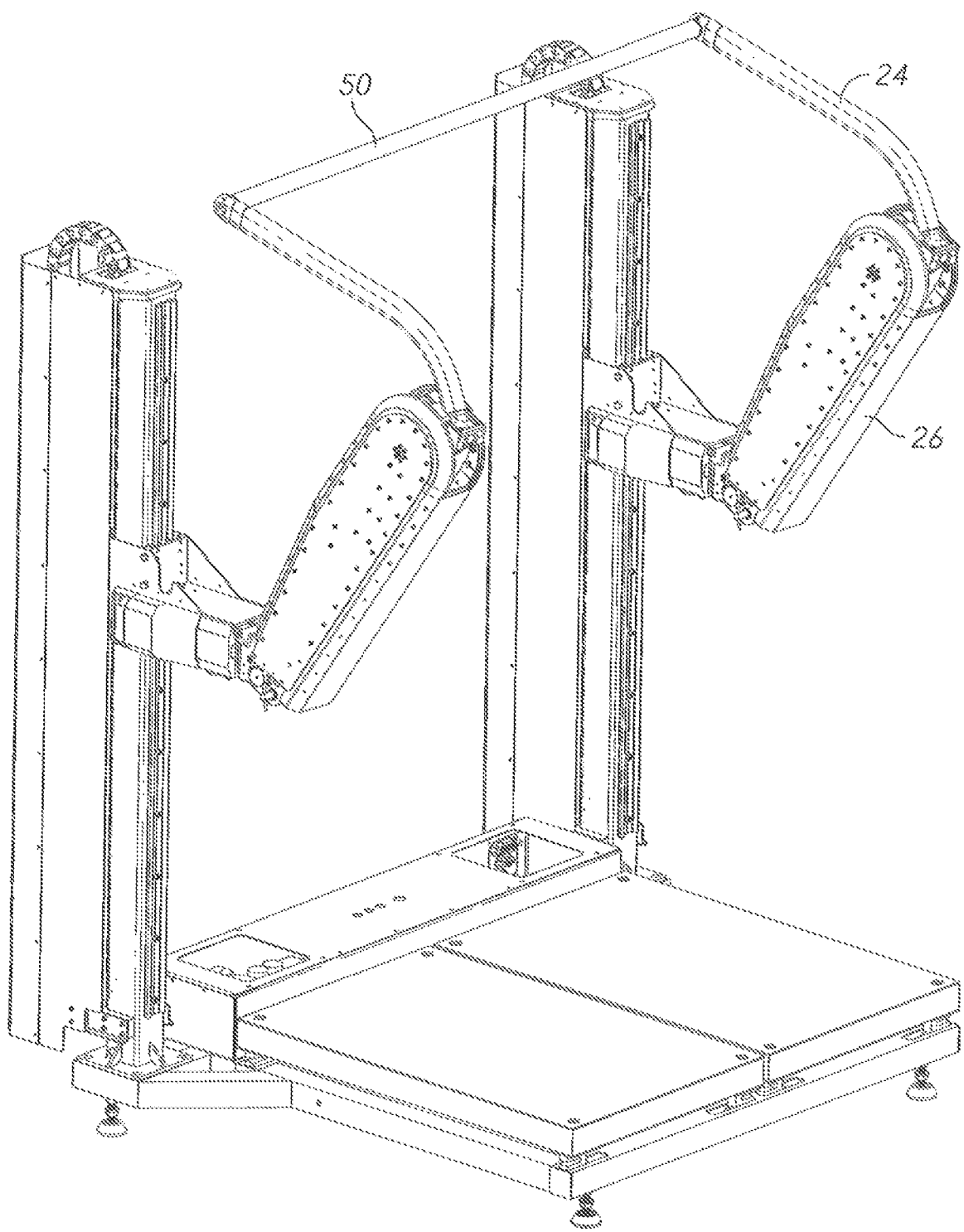
FIG. 24 is a perspective view, showing the embodiment of FIG. 13 with the bar in an elevated position.

It is desirable to provide an embodiment that accommodate a wide variety of exercises and a wide variety of users. FIGS. 23 and 24 show an additional embodiment that is capable of a significant height variation. In FIG. 23, the user will note the provision of right/extended column 104 and left/extended column 106. These are significantly taller than the columns provided in the embodiment of FIG. 1.

Right traveling mount 112 moves up and down on right/extended column 104. Likewise, left traveling mount 114 moves up and down on left/extended column 106. The position of the traveling mounts can be altered and then fixed. Screw drives are a good method of accomplishing this task.

Right/lower link 64 is attached to right traveling mount 112. A U-joint can be used for this connection (similar to the 2-axis U-joint shown in FIG. 3). In some embodiments a simple pivot joint can be used (though this approach sacrifices the ability to move bar 50 laterally). Right/upper link 68 is pivotally connected to right/lower link 64 as for the prior embodiments (using a powered joint).

In an analogous fashion, left/lower link 26 is pivotally connected to left/traveling mount 114. Left/upper link 24 is pivotally connected to left/lower link 26—again using a powered joint. Bar 50 spans the upper portion of the two upper links. This version uses two separate force plates 108, 110. FIG. 24 shows the same embodiment with bar 50 raised to an elevated position. The reader will note how the provision of the extended columns permits bar 50 to travel to a higher position than is possible for the embodiment of FIG. 1.

Returning now to the embodiment of FIG. 2, some general observations about the operation of this embodiment can be made. First the pivotal connection between the lower portion of the lower links and the tops of the columns is preferably made via a universal joint. Second, the connection between each end of bar 50 and its respective upper link is also made via a universal joint (a ball-and-socket joint in the example provided). The degrees of freedom provided therefore allow bar 50 to tilt with respect to base 46. The bar can also move from side to side with respect to the base. Fewer degrees of freedom can be provided if one is willing to forego the lateral motion of the bar or the tilting motion of the bar. It is also possible to provide additional degrees of freedom if one wishes to allow the bar to move even more freely—such as the sliding joints 100, 102 provided in the embodiment of FIG. 21.

The use of a programmable control system allows many different modes of operation. FIGS. 14 and 15 serve to illustrate one example. FIG. 14 shows user 10 in the "high" position for a squat exercise. The user sinks to a low position and then returns to the high position to complete the exercise. Physical therapists often wish to limit the flexion of the knee in a loaded state. FIG. 15 shows the low position. The user shown has a degree of flexion that is beyond what a physical therapist would use in a rehabilitation setting (at least for a loaded state). The control system can be set to eliminate all applied force once bar 50 sinks below a defined height above force plate 48. The user could sink lower if he or she desires, but it would be in an unloaded state. Once the user again lifts the bar above the defined height, the force is reapplied. This height may be referred to as the "force onset height." A maximum height for force-application can also be defines.

Many more features can be found in the various embodiments of the invention. These include:

1. The limit of having a single actuator per side is that the force can only be in one direction. To generate an arbitrary force in a plane, an additional actuator can be added between the lower links and the column caps, replacing the passive universal joints. With these two actuators on the lower link, a force vector in the plane of the actuator can be produced. This allows for the generation of force fields and arbitrary neutral force paths.

2. For the embodiment of FIG. 21, as the user moves the bar forward and backward, the lower joint will move on the slide to keep the distance between the lower joint and the end effector minimized, thus keeping the force vertical.

3. The function of the device is agnostic to the type of actuator that is used. The only requirement for the actuator is that is can produce an accurate torque based on the commanded torque. In order to produce an accurate output torque, the actuator can operate in either open-loop or closed-loop mode. To produce an accurate torque in open-loop mode, a dynamic model of the relationship between control signal and torque must be created that accurately characterizes the system. To operate in closed-loop mode, the actuator must include a torque or force sensing element, which measure the torque that the actuator is applying. In this mode, the sensed torque is compared to the desired torque and then used to adjust the control signal to the actuator.

4. One style of actuator is called the Linear Linkage Actuator. This actuator features an internal mechanism to transfer the torque from the motor to the output via a ball screw and linkage system. This type of actuator is described more fully in U.S. patent application Ser. No. 15/237,793, which is hereby incorporated by reference. Another type of actuator features a motor and a series of one or more speed reducers, which can be a set of pulleys with belts, cables, or chains.

5. The system can reproduce one of many resistance-type exercises. These exercises can be performed standing (e.g. squats, curls, deadlift, etc.) or sitting (bench press, inclined press, seated rows, etc.). The device features two arms, positioned on either side of the device. The arms can be connected with a bar to perform bar style exercise, such as squats. The bar can also be removed and replaced with individual hand grips. In this configuration, the user can perform left and right arm exercises at the same time, or use just one of the device's arms and perform single arm at a time exercises.

6. To accommodate various user heights and various exercises, the vertical position of the lower joint might need to be adjusted to keep the range of motion of the device inside of the range of motion of the user for that particular exercise. The lower joint can be mounted on a mechanism that can raise or lower the position of the lower joint. This motion can be motorized, or can be unpowered, requiring the user to make the adjustment manually. If the motion is motorized, the position can be controlled by the control system of the device. The settings for a given user and exercise can be stored and then the device can automatically adjust the height of the lower joint based on these stored settings. One type of adjustment mechanism is telescoping tubes. Another type of mechanism is a scissor type lift.

7. The user will preferably control the device through a screen and input device. The input could be a mouse and keyboard or a touchscreen. The screen will display relevant settings about the exercise to let the user change the various exercise settings. During the exercise, the screen can display relevant information in real-time about the exercise. This information can include feedback on the center of pressure measurement, the pose of the user from the motion capture system, heart rate, power, speed, force, etc. A video stream of the user can also be augmented with graphical information as determined by the computer, such as user skeleton calculation, bar force vector, weak points of the motion, etc. The screen can also display information to guide the user's motion.

8. The user will preferably also be able to control the device during the exercise from a set of buttons within reach of the user's fingers. These buttons can be mounted on the bar for exercises such as squat or curls. The buttons can be connected to the computer system through either a wire or wireless connection. The buttons can be used for things such as allowing the user to start or stop the exercise, or increase or decrease the load. The system can also be controlled through voice with a microphone via voice-command input to the control system. The invention can also be controlled through physical gestures made by the user with a motion capture system monitoring the user's motion.

9. For safety, the bar can also include a user contact sensor. This will determine if the user releases the bar or hand grip, in which case the system will remove the load from the actuators. The control software can also incorporate a speed of motion limitation.

10. The device can have a single force plate which the user stands on, that can measure the total load and the center of pressure of the load. OR, the force plate can be split into two independent force plates, one for the left foot, and one for the right foot, which each plate able to measure the total load and the center of pressure for the plate.

11. The user's pose can be assessed in real-time via various sensors that feed information to the control system. Form the pose, the skeleton, or joint positions, of the user can be calculated using software algorithms. There are several possible sensors to accomplish the motion tracking, including one or more single lens cameras, one or more stereo cameras, depth cameras (structured light or time of flight), markerless motion capture (IMU), and marker based motion capture. Software will process the data from the motion capture system to produce an estimate of the user's body position, including joint angles, in real time.

12. The motion tracking can be used to confirm the type of exercise that the user is performing. The motion tracking data can also be used to analyze the motion of the user to determine correct and incorrect form.

13. Utilizing the sensor data from the force plate and the user's pose from the motion capture, an algorithm can be written to predict or detect the user's loss of balance during exercises in which the user is standing. The algorithm will use the center of pressure position data to calculate the velocity and acceleration of the center of pressure and also establish a normal position and movement pattern of the center of pressure. The algorithm will also track the motion of the user and compare it to a standard motion and the user's typical motions for the given exercises. From this data, the algorithm can predict that the user will lose balance or determine that the user has already lost balance. In either case, the control system can take immediate action to prevent the user from falling. This can include immediately reducing or removing the load applied to the user.

14. There are preferably position sensors on all active and passive motions of the device. From the position data, the velocity and acceleration of the endpoint of the mechanical interface between the user and the device can be calculated.

15. The device will also be able to integrate with a range of physiological sensors. This can include heart rate, blood pressure, oxygen saturation, respiration rate, and body temperature. These sensors can have a wired or wireless connection to the computer.

16. Calculation of Force: The commanded force to the actuator is determined by the onboard software-based control system.

17. The output force on each side can be adjusted hundreds of times per seconds by the computer algorithm. This allows smooth transitions.

18. The force can be a function of many things, including (a) Desired force by the user, (b) Desired force adjusted depending on eccentric or concentric motion of the user, (c) The user's physiological sensed data (heart rate, heart rate variability, reparation rate, galvanic skin response, etc.), (d) The user's pose, (e) The number of repetitions, (f) The speed at which the user is moving the bar (e.g. if stall is detected, the force can be lowered), (g) The biomechanical muscle length, (h) The acceleration of the bar or other endpoint to simulate inertial forces, and (i) The velocity of the bar or endpoint to simulate viscous forces 19. In addition to the software desired force, a perturbation force can be applied. This perturbation force is a short duration force which occurs in a random or apparently random fashion based on a predetermined probability. This perturbation mode can be used is an assessment tool or a training tool. As an assessment, the response of the user to the series of perturbations is recorded. The response can consist of motion of the user, motion of the user's center of pressure, and motion of the bar. The pattern of perturbations can be stored and applied during assessment sessions with the same user, thus being able to track the user's response to identical (yet seemingly random) perturbations over time.

20. Instead of operating in mode where the applied force is specified, the device can operate where the desired position is specified and the force the user is applying is measured. This mode is referred to as isometric (where the desired position is not changing) or isokinetic (where the desired position is changing at a constant rate). These modes are used to assess the strength of the user.

21. The device can be used to detect or highlight muscle weakness in certain positions, muscle injury, or muscle impairment. By monitoring the position, velocity, acceleration, and power during force controlled motions, the evolution of the data pattern can be compared to healthy patterns to determine an abnormal behavior. By comparing left and right patterns, compensatory movements and motions can also be identified.

22. Blood Flow Restriction (BFR) is a form of exercise where the blood flow to the extremities is restricted. The inventive exercise device can be used in conjunction with BFR exercise to control the pressure in the cuffs that are used to restrict the blood flow. In BFR exercises, completing the desired number of repetitions can be more important than the resistance weight. Therefore, during BFR exercises, the device can monitor the user's motion and reduce the weight in order to ensure that the user complete the proscribed number of repetitions.

23. The inventive device can record, store, and upload all of the data that constitutes an exercise. This includes, the motion of the device, the motion of the user, video of the user, and any physiological data of the user. Facial recognition algorithms can be used to automatically identify the user and link the data to all of the previous data sets for that user. After a set of exercises, the user's data can be processed and analyzed. Various algorithms can be utilized to look for improvements or reductions in performance, muscle weakness or injury, and other conditions. This data can also but uploaded to a cloud server for remote analysis by a human trainer or artificial intelligence algorithm.

The preceding description contains significant detail regarding the novel aspects of the present invention. It is should not be construed, however, as limiting the scope of the invention but rather as providing illustrations of the preferred embodiments of the invention. Many other variations are possible, and the drawings presented depict only a few of these possible variations. Thus, the scope of the invention should be fixed by the claims, rather than by the examples given.

Having described our invention, we claim:

1. An exercise device allowing a user to perform a variety of exercises, comprising:
   (a) a right/column;
   (b) a left/column;
   (c) a right/lower link connected to said right/column by a right/lower universal joint;
   (d) a left/lower link connected to said left/column by a left/lower universal joint;
   (e) a right/upper link connected to said right/lower by a right/powered pivot joint;
   (f) a left/upper link connected to said left/lower by a left/powered pivot joint;
   (g) a bar, having a left end and a right end;
   (h) said right end of said bar being connected to said right/upper link by a right/upper universal joint;
   (i) said left end of said bar being connected to said left/upper link by a left/upper universal joint; and
   (j) a control system configured to selectively vary a first torque applied to said right/powered pivot joint and a second torque applied to said left/powered pivot joint.

2. The exercise device as recited in claim 1, further comprising:
   (a) a base connected to said right/column and said left/column; and
   (b) a force plate mounted on said base, said force plate being configured to measure a reaction force produced by said user.

3. The exercise device as recited in claim 2, wherein said control system uses said reaction force to determine an instantaneous center of pressure for said user.

4. The exercise device as recited in claim 3, wherein:
   (a) said control system uses said instantaneous center of pressure to determine a balance state of said user; and
   (b) said control system is configured to remove said first and second torques in the even that said user enters an unbalanced state.

5. The exercise device as recited in claim 2, wherein:
   (a) said force plate is split into a left force plate and a right force plate; and
   (b) said control system determines an left instantaneous center of pressure of said left force plate and a right instantaneous center of pressure for said right force plate.

6. The exercise device as recited in claim 1, further comprising:
   (a) a right counterbalance mechanism applying a counterbalancing force across said right/lower universal joint; and
   (b) a left counterbalance mechanism applying a counterbalancing force across said left/lower universal joint.

7. The exercise device as recited in claim 6, wherein:
   (a) said right counterbalance mechanism includes,
      (i) a right/cam sheave connected to said right/lower link,
      (ii) a right/cable having a first end and a second end,
      (iii) a right/spring,
      (iv) said first end of said right/spring being configured to move with said right/lower link,
      (v) said right/cable passing around said right/cam sheave, and
      (vi) said second end of said right/cable being connected to said right/spring;
   (b) said left counterbalance mechanism includes,
      (i) a left/cam sheave connected to said left/lower link,
      (ii) a left/cable having a first end and a second end,
      (iii) a left/spring,
      (iv) said first end of said left/spring being configured to move with said left/lower link,
      (v) said left/cable passing around said left/cam sheave, and
      (vi) said second end of said left/cable being connected to said left/spring.

8. The exercise device as recited in claim 1, wherein said control system monitors a torque and a position of said right/powered joint and said left/powered joint.

9. The exercise device as recited in claim 2, wherein said control system monitors a torque and a position of said right/powered joint and said left/powered joint.

10. The exercise device as recited in claim 3, wherein said control system monitors a torque and a position of said right/powered joint and said left/powered joint.

11. An exercise device allowing a user to perform a variety of exercises, comprising:
    (a) a right/column;
    (b) a left/column;
    (c) a right/carrier connected to said right/column by a right/first pivot joint;
    (d) a left/carrier connected to said left/column by a left/first pivot joint;
    (e) a right/lower link connected to said right/carrier by a right/second pivot joint;
    (f) a left/lower link connected to said left/carrier by a left/second pivot joint;
    (g) a right/upper link connected to said right/lower by a right/powered pivot joint;
    (h) a left/upper link connected to said left/lower by a left/powered pivot joint;
    (i) a bar, having a left end and a right end;
    (j) said right end of said bar being connected to said right/upper link by a right/upper universal joint;
    (k) said left end of said bar being connected to said left/upper link by a left/upper universal joint; and
    (l) a control system configured to selectively vary a first torque applied to said right/powered pivot joint and a second torque applied to said left/powered pivot joint.

12. The exercise device as recited in claim 11, further comprising:
    (a) a base connected to said right/column and said left/column; and
    (b) a force plate mounted on said base, said force plate being configured to measure a reaction force produced by said user.

13. The exercise device as recited in claim 12, wherein said control system uses said reaction force to determine an instantaneous center of pressure for said user.

14. The exercise device as recited in claim 13, wherein:
    (a) said control system uses said instantaneous center of pressure to determine a balance state of said user; and
    (b) said control system is configured to remove said first and second torques in the even that said user enters an unbalanced state.

15. The exercise device as recited in claim 12, wherein:
(a) said force plate is split into a left force plate and a right force plate; and
(b) said control system determines an left instantaneous center of pressure of said left force plate and a right instantaneous center of pressure for said right force plate.

16. The exercise device as recited in claim 11, further comprising:
(a) a right counterbalance mechanism applying a counterbalancing force across said right/first pivot joint; and
(b) a left counterbalance mechanism applying a counterbalancing force across said left/first pivot joint.

17. The exercise device as recited in claim 16, wherein:
(a) said right counterbalance mechanism includes,
    (i) a right/cam sheave connected to said right/lower link,
    (ii) a right/cable having a first end and a second end,
    (iii) a right/spring,
    (iv) said first end of said right/spring being configured to move with said right/lower link,
    (v) said right/cable passing around said right/cam sheave, and
    (vi) said second end of said right/cable being connected to said right/spring;
(b) said left counterbalance mechanism includes,
    (i) a left/cam sheave connected to said left/lower link,
    (ii) a left/cable having a first end and a second end,
    (iii) a left/spring,
    (iv) said first end of said left/spring being configured to move with said left/lower link,
    (v) said left/cable passing around said left/cam sheave, and
    (vi) said second end of said left/cable being connected to said left/spring.

18. The exercise device as recited in claim 11, wherein said control system monitors a torque and a position of said right/powered joint and said left/powered joint.

19. The exercise device as recited in claim 12, wherein said control system monitors a torque and a position of said right/powered joint and said left/powered joint.

20. The exercise device as recited in claim 13, wherein said control system monitors a torque and a position of said right/powered joint and said left/powered joint.

* * * * *